United States Patent [19]

Crounse et al.

[11] 4,189,171
[45] Feb. 19, 1980

[54] MARKING SYSTEMS CONTAINING 3-ARYL-3-HETERYLPHTHALIDES AND 3,3-BIS(HETERYL)PHTHALIDES

[75] Inventors: Nathan N. Crounse, Cincinnati; Paul J. Schmidt, Sharonville, both of Ohio

[73] Assignee: Sterling Drug Inc., New York, N.Y.

[21] Appl. No.: 868,583

[22] Filed: Jan. 11, 1978

Related U.S. Application Data

[63] Continuation-in-part of Ser. No. 773,180, Mar. 1, 1977, abandoned.

[51] Int. Cl.² .................. B41L 1/36; B41M 5/16; B41M 5/18
[52] U.S. Cl. .................. 282/27.5; 260/315; 260/326.14 R; 260/326.37; 427/144; 427/148; 427/150; 427/151; 427/261; 428/307; 428/913; 428/914
[58] Field of Search ........... 282/27.5; 427/144, 148, 427/150, 151, 261; 428/913, 914, 307; 96/3; 260/326.14 R, 315, 326.37

[56] References Cited

U.S. PATENT DOCUMENTS

| | | | |
|---|---|---|---|
| 3,427,971 | 2/1969 | Steber et al. | 427/144 |
| 3,491,111 | 1/1970 | Lin | 260/315 |
| 3,491,116 | 1/1970 | Lin | 260/326.14 |
| 3,509,173 | 4/1970 | Lin | 260/326.14 R |
| 3,509,174 | 4/1970 | Lin | 282/27.5 X |
| 3,774,539 | 11/1973 | Miyazaua et al. | 427/144 X |
| 3,779,753 | 12/1973 | Bloom et al. | 96/3 |
| 3,792,481 | 2/1974 | Nagashima et al. | 427/144 X |
| 3,924,041 | 12/1975 | Miyayama et al. | 427/148 X |
| 3,962,526 | 6/1976 | Panken | 427/144 X |
| 4,094,877 | 6/1978 | Crounse et al. | 428/307 X |
| 4,491,112 | 1/1970 | Lin | 282/27.5 X |

FOREIGN PATENT DOCUMENTS 850359  7/1977  Belgium.

*Primary Examiner*—Thomas J. Herbert, Jr.
*Attorney, Agent, or Firm*—Terrence E. Miesle; Lynn T. Fletcher; B. Woodrow Wyatt

[57] ABSTRACT

3-Aryl-3-indolylphthalides, 3-aryl-3-pyrrolylphthalides and 3-aryl-3-carbazolylphthalides prepared by interaction of the appropriate 2-(heteroaryl)carbonylbenzoic acid and the appropriate phenylamine, and 3,3-bis(indolyl)phthalides prepared by the interaction of the appropriate 2-(indolyl)carbonylbenzoic acid and the appropriate indole are useful as color formers in pressure-sensitive carbonless duplicating systems, thermal marking systems and hectographic copying systems.

15 Claims, No Drawings

MARKING SYSTEMS CONTAINING 3-ARYL-3-HETERYLPHTHALIDES AND 3,3-BIS(HETERYL)PHTHALIDES

This application is a continuation-in-part of our prior copending application Ser. No. 773,180, filed Mar. 1, 1977, now abandoned.

BACKGROUND OF THE INVENTION (a) Field of the Invention

This invention relates to novel compounds classified in the field of organic chemistry as 3-aryl-3-heteroarylphthalides and 3,3-bis (heteroaryl)phthalides useful as color precursors, particularly in the art of carbonless duplicating as, for example, in pressure-sensitive systems, in thermal marking systems and in hectographic or spirit-reproducing copying systems; to substituted 2-(indolylcarbonyl) benzoic acids and 2-(pyrrolylcarbonyl) benzoic acids useful as intermediates to the subject phthalide color precursors; to processes for preparing said phthalides and benzoic acids; and to pressure-sensitive duplicating systems, thermal marking systems and hectographic copying systems containing the same.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides with which this invention is concerned, for example, crystal violet lactone; fluorans, for example, 2'-anilino-6'-diethylaminofluran and 2'-dibenzylamino-6'-diethylaminofluoran; and various other types of colorless precursors currently employed in commercially accepted carbonless copy systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art suffer one or more disadvantage such as low tinctorial strength, poor light stability, low resistance to sublimation, low susceptibility to copiability of the color-developed form in standard copying machines, for example, a Xerox copier, and low solubility in common organic solvents, the latter disadvantage thus requiring the use of specialized and expensive solvents in order to obtain microencapsulated solutions of sufficient concentration for use in pressure-sensitive copying systems.

The following items to date appear to constitute the most relevant prior art with regard to the instant invention.

U.S. Pat. No. 3,491,112, issued Jan. 20, 1970 discloses in most pertinent part of series of normally colorless phthalides stated to be useful as color formers in pressure-sensitive copying paper which are represented by the structural formula

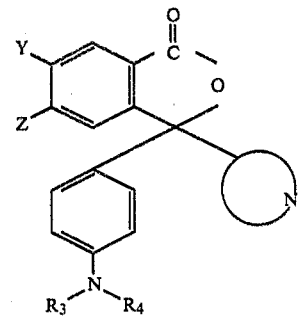

wherein

is a heterocyclic radical selected from the group consisting of

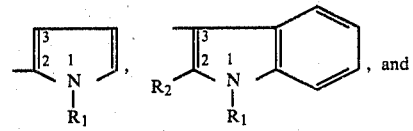

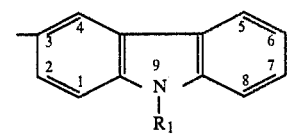

in which $R_1$ and $R_2$ are $C_1$ to $C_4$ alkyl, phenyl and hydrogen; Z and Y are hydrogen and dialkylamino in which alkyl is $C_1$ to $C_4$ alkyl with the proviso that only one Z and Y can be said dialkylamino while the other is hydrogen; and $R_3$ and $R_4$ are $C_1$ to $C_4$ alkyl.

U.S. Pat. No. 3,779,753, issued Dec. 18, 1973 discloses the phthalide having the formula

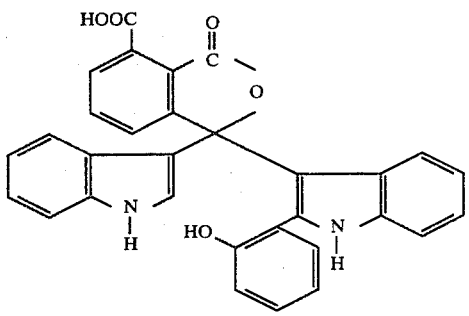

which is stated to be useful as an optical filter agent in photographic processes to protect a selectively exposed photosensitive material from further exposure during processing in the presence of incident light.

British Patent Specification No. 1,427,318, published Mar. 10, 1976, discloses the interaction of trimellitic anhydride and m-diethylaminophenol to obtain a mixture of 4-diethylamino-2-hydroxybenzophenone-2', 4'-dicarboxylic acid and the corresponding 2', 5'-dicarboxylic acid isomer. The isomeric mixture is then interacted with 3,5-dimethylphenol in the presence of sulfuric acid followed by treatment with sodium hydroxide to obtain the compound having the structure

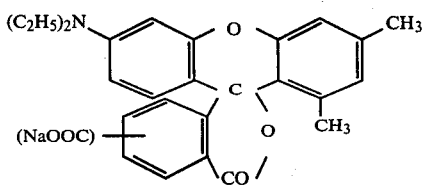

which is stated to be useful as a color former in a spirit reproducing process.

U.S. Pat. No. 3,509,174, issued Apr. 28, 1970, discloses 1,2-dimethyl-3-(2-carboxybenzoyl)indole which is stated to be an intermediate to a series of 3,3-bis (3-indolyl)phthalides useful as color formers in pressure-sensitive copying paper.

SUMMARY OF THE INVENTION

The present invention provides novel 3-aryl-3-heteroarylphthalides selected from among 3-aryl-3-indolyphthalides, 3-aryl-3-pyrrolylphthalides, 3-aryl-3-carbazolylphthalides and 3,3-bis(heteroaryl)phthalides, particularly 3,3-bis(indolyl)-phthalides which are useful as color formers in pressure-sensitive duplicating systems, in thermal marking systems and in hectographic or spirit-reproducing systems. The compounds develop colored images of good to excellent tinctorial strength, and have the advantages of improved light stability, high resistance to sublimation and enhanced solubility in common organic solvents. Certain species are also soluble in water and lower alcohols and are therefore of particular utility as color formers in hectographic or spirit-reproducing copying systems. The present invention also provides 2-heteroarylcarbonyl benzoic acids useful as intermediates to the subject phthalide color formers.

In one of its composition of matter aspects the invention relates to a series of 3-aryl-3-heteroaryl-4-R°-5-R$^1$-6-R$^2$-7-R$^3$-phthalides and 3,3-bis(heteroaryl)-4-R°-5-R$^1$-6R$^2$-7-R$^3$-phthalides which are useful as color formers in pressure-sensitive carbonless duplicating systems, thermal marking systems or hectographic copying systems.

In a second of its composition of matter aspects, the invention relates to certain 2-heteroaryl-carbonyl-3-R°-4-R$^1$-5-R$^2$-6-R$^3$-benzoic acids which are useful as intermediates for the preparation of the phthalide final products of the invention.

In one of its process aspects, the invention relates to a process for preparing a 3-X-3-Z-4-R°-5-R$^1$-6-R$^2$-7-R$^3$-phthalide which comprises interacting a 2-(X-carbonyl)-3-R°-4-R$^1$-5-R$^2$-6-R$^3$-benzoic acid with a 3-R$^4$-N,N-(R)$_2$-aniline or a 1--R$^{6'}$-2-R$^{5'}$-5/6-Y$^{1'}$-indole.

In a second process aspect, the invention relates to a process for preparing a 3-X-3-Z-5/6-aminophthalide which comprises reducing the corresponding 3-X-3-Z-5/6-nitrophthalide.

In a third process aspect, the invention relates to a process for preparing a 3-X-3-Z-5/6-acetamidophthalide which comprises interacting the appropriate 2-(X-carbonyl)-5/6-aminobenzoic acid with a 3-R$^4$-N,N-(R)$_2$-aniline or a 1-R$^{6'}$-2-R$^{5'}$-5/6-Y$^{1'}$-indole in the presence of acetic anhydride.

In a fourth process aspect, the invention relates to a process for preparing a 3-X-3-Z-5/6-COOY-phthalide which comprises esterifying the corresponding 3-X-3-Z-5/6 carboxyphthalide with an appropriate alkylating agent in the presence of an alkali.

In a fifth process aspect, the invention relates to a process for preparing a 3-X-3-Z-5/6-CONY'Y'-phthalide which comprises amidating the corresponding 3-X-3-Z-5/6-carboxyphthalide with the appropriate compound of the formula HNY'Y'''.

In a sixth process aspect, the invention relates to a process for preparing a 3-[(1-R$^6$-2-R$^5$-5/6-Y$^1$ ) -3-indolyl]-3-[(1-R$^{6'}$-2-R$^{5'}$-5/6-Y$^{1'}$)-3-indolyl]-4-R°-5-R$^1$-6-R$^2$-7-R$^3$-phthalide in which R$^5$=R$^{5'}$, R$^6$ =$^{R6'}$ and Y$^1$ =Y$^{1'}$ which comprises interacting a 3-R°-4-R$^1$-5-R$^2$-6-R$^3$-phthalic anhydride with approximately two molecular proportions of a 1-R$^6$-2-R$^5$-5/6-Y$^1$-indole.

In a seventh process aspect, the invention relates to a process for preparing a 2-(X-carbonyl)-3-R°-4-R$^1$-5-R$^2$-6-R$^3$ benzoic acid which comprises interacting a 3-R°-4-R$^1$-5-R$^2$-6-R$^3$-phthalic anhydride with a 1-R$^6$-2-R$^5$-5/6-Y$^1$ -indole or a 1-R$^7$-pyrrole.

In an eighth process aspect, the invention relates to a process for preparing a 2-(X-carbonyl)-5/6-aminobenzoic acid which comprises reducing the corresponding 2-(X-carbonyl)-5/6-nitrobenzoic acid.

The present invention provides as articles of manufacture pressure-sensitive carbonless duplicating systems, thermal marking systems and hectographic copying systems each containing a color-forming substance comprising a 3-aryl-3-heteroaryl-4-R°-5-R$^1$-6-R$^2$-7-R$^3$-phthalide or a 3,3-bis (heteroaryl)-4-R°-5-R$^1$-6-R$^2$-7-R$^3$-phthalide.

DETAILED DESCRIPTION INCLUSIVE OF THE PREFERRED EMBODIMENTS

More specifically, this invention, in one of its composition of matter aspects relating to the final products, resides in the novel phthalides, which are particularly useful as colorless precursors in the art of carbonless duplicating, thermal marking and hectograph duplicating, and which are selected from the group consisting of 3-X-3-Z-4-R°-5-R$^1$-6-R$^2$-7-R$^3$-phthalides having the formula

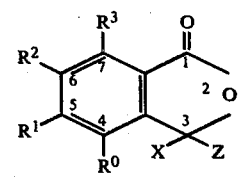

Formula I wherein R°, R$^1$, R$^2$ and R$^3$ each represent hydrogen or halo or when R°, R$^3$ and one of R$^1$ and R$^2$ are each hydrogen, the other of R$^1$ and R$^2$ represents nitro, amino, acetamido, dialkylamino wherein alkyl is non-tertiary C$_1$ to C$_4$ alkyl or

in which B represents -OY or

wherein Y is hydrogen, an alkali metal cation, an ammonium cation, a $C_1$ to $C_{18}$ mono-, di- or trialkylammonium cation, $C_2$ to $C_{18}$ alkyl, $C_2$ to $C_{18}$ alkenyl, benzyl or benzyl substituted in the benzene ring thereof by $C_1$ to $C_{12}$ alkyl, halo or $C_1$ to $C_8$ alkoxy; Y' is hydrogen or $C_1$ to $C_{18}$ alkyl; Y" is hydrogen, $C_1$ to $C_{18}$ alkyl or $C_4$ to $C_{12}$ N,N-dialkylaminoalkyl; X represents a monovalent moiety selected from the class having the formulas

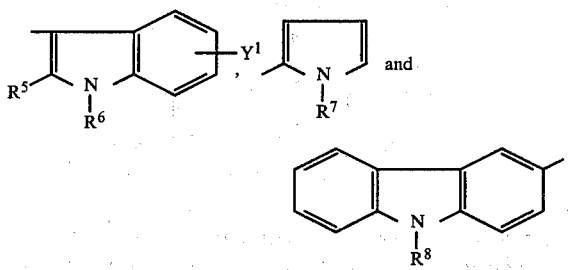

Z represents a monovalent moiety selected from the class having the formulas

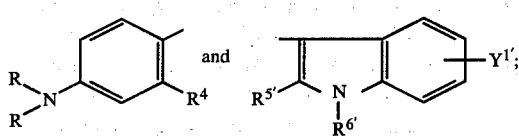

where, in the above, R represents non-tertiary $C_1$ to $C_4$ alkyl, benzyl or benzyl substituted in the benzene ring by one or two of halo or $C_1$ to $C_3$ alkyl, $R^4$ represents acetamido, dialkylamino in which alkyl is non-tertiary $C_1$ to $C_4$ alkyl, and when one of $R^1$ or $R^2$ represents any of said carboxy or said carbonyl substituents, $R^4$ further represents hydrogen, $C_1$ to $C_3$ alkyl, $C_1$ to $C_4$ alkoxy or halo, $R^5$ and $R^{5'}$ represent hydrogen, $C_1$ to $C_3$ alkyl or phenyl, $R^6$ represent hydrogen, $C_1$ to $C_{18}$ alkyl, $C_2$ to $C_4$ alkenyl, benzyl or benzyl substituted in the benzene ring by one of two of halo or $C_1$ to $C_3$ alkyl, $R^7$ and $R^8$ represent hydrogen, $C_1$ to $C_3$ alkyl or phenyl, and $Y^1$ represent one or two of hydrogen, $C_1$ to $C_3$ alkyl, $C_1$ to $C_3$ alkoxy, halo or nitro with the provisos (i) that X and Z can both simultaneously represent monovalent indolyl moieties only when at least one of $R^1$ and $R^2$ represent said

(ii) X represents a pyrrolyl or a carbazolyl moiety only when Z represents a 2-$R^4$-4-N(R)$_2$-phenyl moiety.

In a first particular embodiment in accordance with its final product composition of matter aspect, the invention sought to be patented resides in the novel 3-[2-$R^4$-N(R)$_2$-phenyl]-3-X-4-$R^\circ$-5-$R^1$-6-$R^2$-7-$R^3$-phthalides of Formula I wherein Z is 2-$R^4$-4-N(R)$_2$ phenyl and are of the formula

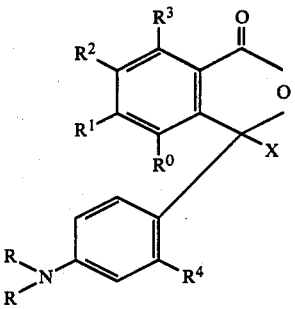

wherein R, $R^\circ$, $R^2$, $R^3$, $R^4$ and X each have the same respective meanings given in relation to Formula I. Preferred compounds within the ambit of this particular embodiment are: the novel 3-[2-$R^4$-4-N(R)$_2$-phenyl]-3-[(1-$R^{62}$-$R^5$-5/6-$Y^1$ ) -3-indolyl]-4-$R^\circ$-5-$R^1$-6-$R^2$-7-$R^3$-phthalides of Formula II wherein X is 1-$R^6$-2-$R^5$-5/6-$Y^1$-3-indolyl according to the formula

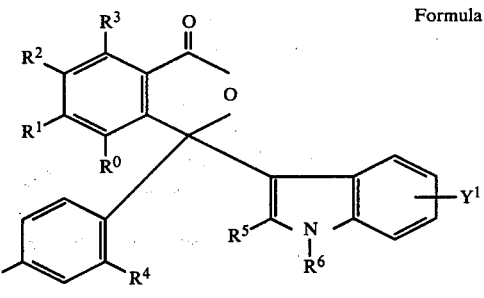

wherein R, $R^\circ$, $R^1$, $R^2$, $R^3$, $R^4$, $R^5$, $R^6$ and $Y^1$ each have the same respective meanings given in relation to Formula II; the novel 3-[2-$R^4$-4-N(R)$_2$-phenyl]-3-(1-$R^7$-2-pyrrolyl)-4-$R^\circ$-5-$R^1$-6-$R^2$-7-$R^3$-phthalides of Formula II wherein X is 1-$R^7$-2-pyrrolyl according to the formula

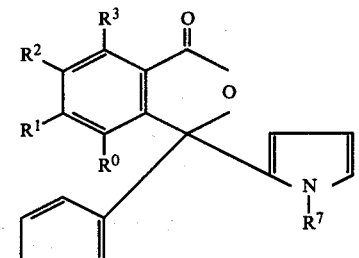

wherein R, $R^\circ$, $R^1$, $R^2$, $R^3$, $R^4$ and $R^7$ each have the same respective meanings given relation to Formula II; and the novel 3-[2-$R^4$-4-N(R)$_2$-phenyl]-3-(9-$R^8$-3-carbazoyl)-4-$R^\circ$-5-$R^1$-6-$R^2$-7-$R^3$-phthalides of Formula II wherein X is 9-$R^8$-3-carbazolyl according to the formula

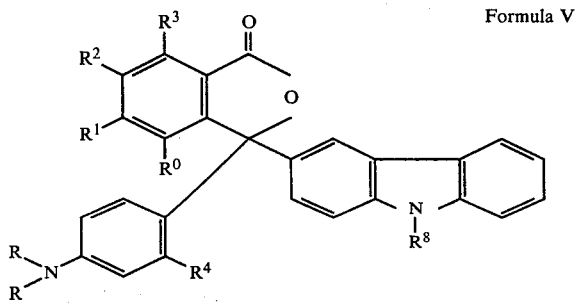

Formula V

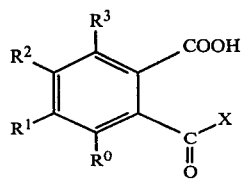

wherein R, R°, R¹, R², R³, R⁴ and R⁸ each have the same respective meanings given in relation to Formula II.

In a second particular embodiment in accordance with its final product composition of matter aspect, the invention sought to be patented resides in the novel 3-[(1-R⁶-2-R⁵-5/6-Y¹ )-3-indolyl]-3-[(1-R⁶'-2-R⁵'-5/6-Y¹'-3-indolyl]-4-R°-5-R¹-6-R²-7-R³-phthalides of Formula I wherein X is 1-R⁶-2-R⁵-5/6-Y¹-3-indolyl and Z is 1-R⁶'-2-R⁵'-5/6-Y¹'-3-indolyl. Preferred compounds within the ambit of this particular embodiment are of the formula

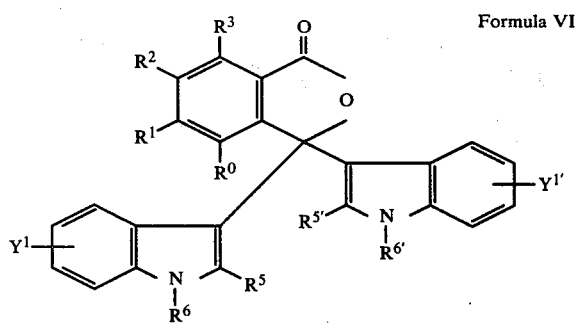

Formula VI wherein the indolyl moieties can be the same or different; R° and R³ and at least one of R¹ and R² represent hydrogen and the other represents

C—B in which B represents —OY or

wherein Y is hydrogen, an alkali metal cation, an ammonium cation, a C₁ to C₁₈ mono-, di- or trialkylammonium cation, C₂ to C₁₈ alkyl, C₂ to C₁₈ alkenyl, benzyl or benzyl substituted in the benzene ring thereof by C₁ to C₁₂ alkyl, halo or C₁ to C₈ alkoxy; Y' is hydrogen or C₁ to C₁₈ alkyl; Y" is hydrogen, C₁ to C₁₈ alkyl or C₄ to C₁₂ N,N-dialkylaminoalkyl; and R⁵, R⁵', R⁶, R⁶', Y¹ and Y¹' each have the same respective meanings given in relation to Formula I.

This invention, in a second of its composition of matter aspects, relating to intermediates, resides in the novel 2-(X-carbonyl)-3-R°-4-R¹-5R²-6-R³-benzoic acids which are useful as intermediates to the final products and having the formula

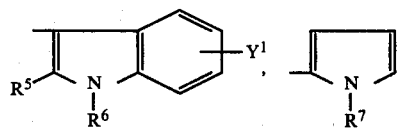

Formula VII wherein R°, R¹, R² and R³ each represent hydrogen, or halo or when R°, R³ and one of R¹ and R² are each hydrogen, the other of R¹ and R² represents amino or carboxy; X represents a monovalent moiety selected from the class having the formulas

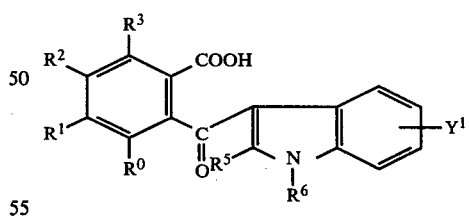

in which R⁵ represents hydrogen, C₁ to C₃ alkyl or phenyl, R⁶ represents C₄ to C₁₈ alkyl, C₂ to C₄ alkenyl, benzyl or benzyl substituted in the benzene ring by one or two of halo or C₁ to C₃ alkyl or represents hydrogen or C₁ to C₃ alkyl only when Y¹ is other than hydrogen and/or when one of R¹ and R² is amino or carboxy; R⁷ represents hydrogen, C₁ to C₃ alkyl or phenyl; and Y¹ represents one or two of hydrogen, C₁ to C₃ alkyl, C₁ to C₃ alkoxy, halo or nitro.

In a first particular embodiment in accordance with its composition of matter aspects relating to intermediates, the invention sought to be patented resides in the novel 2{[(1-R⁶-2-R⁵-5/6-Y¹)-3-indolyl]carbonyl}3-R°-4-R¹-5-R²-6-R³-benzoic acids of Formula VII wherein X is 1-R⁶-2-R⁵-5/6-Y¹-3-indolyl. Preferred compounds within the ambit of this particular embodiment are of the formula Formula VIII wherein R°, R¹, R², R³, R⁵, R⁶ and Y¹ each have the same respective meanings given in relation to Formula VII.

In a second particular embodiment in accordance with its intermediates to final products composition of matter aspect the invention sought to be patented resides in the novel 2-[(1-R⁷-2-pyrrolyl)carbonyl]-3-R°-4-R¹-5-R²-6-R³-benzoic acids of Formula VII wherein X is 1-R⁷-2-pyrrolyl. Preferred compounds within the ambit of this particular embodiment are of the formula

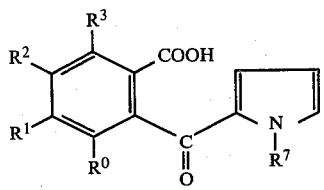

Formula IX wherein R°, R¹, R², R³ and R⁷ each have the same respective meanings given in relation to Formula VII.

In one of its process aspects, the invention sought to be patented resides in the process for preparing a 3-X-3-Z-4-R°-5-R¹-6-R²-7-R³-phthalide according to Formula I which comprises interacting a 2-(X-carbonyl)-3-R°-4-R¹-5-R²-6-R³-benzoic acid with approximately one molecular proportion of a 3-R⁴-N,N-(R)₂-aniline or a 1-R⁶'-2-R⁵'-5/6-Y¹'-indole in the presence of an anhydride of an alkanoic acid having from 2 to 5 carbon atoms wherein R°, R¹, R² and R³ each represent hydrogen or halo or when R°, R³ and one of R¹ and R² are each hydrogen, the other of R¹ and R² represents nitro, dialkylamino wherein alkyl is non-tertiary $C_1$ to $C_4$ alkyl, or carboxy; and R, R⁴, R⁵', R⁶', X, Y¹' and Z each have the same respective meanings given in relation to Formula I.

In a second of its process aspects, the invention sought to be patented resides in the process for preparing a 3-X-3-Z-5/6-aminophthalide according to Formula I which comprises reducing the corresponding 3-X-3-Z-5/6-nitrophthalide wherein X and Z each have the same respective meanings given in relation to Formula I.

In a third of its process aspects, the invention sought to be patented resides in the process for preparing a 3-X-3-Z-5/6-acetamidophthalide according to Formula I which comprises interacting the appropriate 3-(X-carbonyl)-5/6-aminobenzoic acid with approximately one molecular proportion of a 3-R⁴-N,N-(R)₂-aniline or a 1-R⁶'-2-R⁵'-5/6-Y¹'-indole in the presence of at least two molecular proportions of acetic anhydride wherein R, R⁴, R⁵', R⁶', X, Y¹' and Z each have the same respective meanings given in relation to Formula I.

In a fourth of its process aspects, the invention sought to be patented resides in the process for preparing a 3-X-3-Z-5/6-COOY-phthalide according to Formula I in which Y is $C_2$ to $C_{18}$ alkyl, $C_2$ to $C_{18}$ alkenyl, benzyl or benzyl substituted in the benzene ring thereof by $C_1$ to $C_{12}$ alkyl, halo or $C_1$ to $C_8$ alkoxy and X and Z have the same respective meanings given in relation to Formula I which comprises esterifying the corresponding 3-X-3-Z-5/6-COOH-phthalide with an appropriate compound selected from the group consisting of dimethyl sulfate, diethyl sulfate or Y-halogen in which Y is $C_2$ to $C_{18}$ alkyl, $C_2$ to $C_{18}$ alkenyl, benzyl, or benzyl substituted in the benzene ring thereof by $C_1$ to $C_{12}$ alkyl, halo or $C_1$ to $C_8$ alkoxy in the presence of an alkali metal hydroxide or carbonate.

In a fifth of its process aspects, the invention sought to be patented resides in the process for preparing a 3-X-3-Z-5/6-

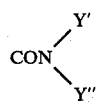

-phthalide according to Formula I in which Y', Y'', X and Z each have the same respective meanings given in Claim 1 which comprises amidating the corresponding 3-X-3-Z-5/6-COOH-phthalide or appropriate carboxylic functional derivative thereof with the appropriate compound of the formula

in which Y' and Y'' each have the same meanings given in relation to Formula I.

In a sixth of its process aspects, the invention sought to be patented resides in the process for preparing a 3-[(1-R⁶-2-R⁵-5/6-Y¹)-3-indolyl]-3-[(1-R⁶'-2-R⁵'-5/6-Y¹')-3-indolyl]-4-R°-5-R¹-6-R²-7-R³-phthalide according to Formula VI in which R⁵=R⁵', R⁶=R⁶' and Y¹=Y¹' which comprises interacting a 3-R°-4-R¹-5-R²-6-R³-phthalic anhydride with approximately two molecular proportions of a 1-R⁶-2-R⁵-5/6-Y¹-indole in the presence of an anhydride of an alkanoic acid having from 2 to 5 carbon atoms wherein R°, R¹, R², R³, R⁵, R⁶, R⁵', R⁶', Y¹ and Y¹' each have the same respective meanings given in relation to Formula VI.

In a seventh of its process aspects, the invention sought to be patented resides in the process for preparing a 2-(X-carbonyl)-3-R°-4-R¹-5-R²-6-R³-benzoic acid according to Formula VII which comprises interacting a 3-R°-4-R¹-5-R²-6-R³-phthalic anhydride with approximately one molecular proportion of a 1-R⁶-2-R⁵-5/6-Y¹-indole or a 1-R⁷-pyrrole in the presence of a Lewis acid wherein R°, R¹, R² and R³ each represent hydrogen or halo or when R°, R³ and one of R¹ and R² are each hydrogen, the other of R¹ and R² represents carboxy and R⁵, R⁶, R⁷, X and Y¹ each have the same respective meanings given in relation to Formula VII.

In an eighth of its process aspects, the invention sought to be patented resides in the process for preparing a 2-(X-carbonyl)-5/6-amino-benzoic acid according to Formula VII which comprises reducing the corresponding 2-(X-carbonyl)-5/6-nitrobenzoic acid wherein X has the same meaning given in relation to Formula VII.

In an article-of-manufacture aspect, the invention sought to be patented resides in a pressure-sensitive carbonless duplicating system, thermal marking system or hectographic copy system containing as a color-forming substance a 3-X-3-Z-4-R°-5-R¹-6-R²-7-R³-phthalide according to Formula I wherein R°, R¹, R², R³, X and Z have the same respective meanings given in relation to Formula I.

A particular embodiment sought to be patented resides in a pressure-sensitive transfer sheet, adapted for use with a receiving sheet having an electron accepting layer, comprising a support sheet coated on one side with a layer of pressure-rupturable microcapsules, said microcapsules containing a liquid solution of a color forming substance comprising at least one compound having Formula I.

Another particular embodiment sought to be patented resides in a heat responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

Preferred articles within the ambit of the particular embodiments above-described are those wherein the color-forming component comprises a 3-[2-$R^4$-4-N(R)$_2$-phenyl]-3-[(1-$R^6$-2-$R^5$-5/6-$Y^1$)-3-indolyl]-4-$R°$-5-$R^1$-6-$R^2$-7-$R^3$-phthalide wherein R, R°, $R^1$, $R^2$, $R^3$, $R^4$, $R^5$, $R^6$ and $Y^1$ have the same respective meanings given in relation to Formula III or a 3-[(1-$R^6$-2-$R^5$-5/6-$Y^1$)-3-indolyl]-3-[(1-$R^{6'}$-2-$R^{5'}$-5/6-$Y^{1'}$)-3-indolyl]-4-$R°$-5-$R^1$-6-$R^2$-7-$R^3$-phthalide wherein R°, $R^1$, $R^2$, $R^3$, $R^5$, $R^6$, $R^{5'}$, $R^{6'}$, $Y^1$ and $Y^{1'}$ have the same respective meanings given in relation to Formula VI.

A further particular embodiment sought to be patented resides in a hectographic or spirit reproducing copying system comprising a transfer sheet coated on one side with a layer containing a color-forming substance comprising a compound according to Formula I wherein R°, $R^3$ and one of $R^1$ and $R^2$ are each hydrogen, the other of $R^1$ and $R^2$ represents

wherein Y is hydrogen, an alkali metal cation, an ammonium cation or a $C_1$ to $C_{18}$ mono-, di- or trialkylammonium cation.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However the other above-named halo substituents are also satisfactory.

The terms "$C_1$ to $C_4$ alkoxy" and "dialkylamino in which alkyl is non-tertiary $C_1$ to $C_4$ alkyl" denote saturated, acyclic groups which may be straight or branched as exemplified by methoxy, ethoxy, propoxy, isopropoxy, butoxy, sec-butoxy, isobutoxy, tert-butoxy, dimethylamino, diethylamino, ethylmethylamino, dipropylamino, dibutylamino, isobutylmethylamino, and the like.

As used herein the terms "$C_1$ to $C_3$ alkyl", "$C_1$ to $C_{12}$ alkyl" and "$C_1$ to $C_{18}$ alkyl" denote saturated monovalent straight or branched aliphatic hydrocarbon radicals including methyl, ethyl, propyl, isopropyl, butyl, isobutyl, tert-butyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl, n-tridecyl, n-tetradecyl, n-pentadecyl, n-hexadecyl, n-heptadecyl, n-octadecyl, 1,3,5-trimethylhexyl, 1,5-dimethyl-4-ethylhexyl, 5-methyl-2-butylhexyl, 2-propylnonyl, 2-butyloctyl, 2-pentylnonyl, 1,2-dimethylhexadecyl, and the like.

As used herein the term "alkali metal cation" includes lithium, sodium and potassium cations.

The term "$C_1$ to $C_{18}$ alkylammonium cation" includes ammonium cations substituted by from 1 to 3 alkyl groups as above described. The alkyl groups can be the same or different provided the ammonium cation contains no more than 18 carbon atoms. As examples there can be named methylammonium, t-butylammonium, t-octylammonium, n-dodecylammonium, n-octadecylammonium, di-n-butylammonium, di-n-nonylammonium, isopropyl-n-butylammonium, dimethyl-n-butylammonium, triethylammonium, N-ethyl-N,N-diisopropylammonium, tributylammonium, di-n-butyl-n-octylammonium and the like.

The terms "$C_1$ to $C_8$ alkoxy and "$C_1$ to $C_{18}$ alkoxy" includes saturated, acyclic, straight or branch-chained groups such as methoxy, ethoxy, propoxy, isopropoxy, butoxy, sec-butoxy, isobutoxy, tert-butoxy, n-pentyloxy, n-hexyloxy, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, 1-methylpentyloxy, 2,2-dimethyl-butyloxy, 2-methylhexyloxy, 1,4-dimethylpentyloxy, 3-ethylpentyloxy, 2-methylheptyloxy, 1-ethylhexyloxy, 2-propylpentyloxy, 2-methyl-3-ethylpentyloxy, 1,3,5-trimethylhexyloxy, 1,5-dimethyl-4-ethylhexyloxy, 5-methyl-2-butylhexyloxy, 2-propylnonyloxy, 2-butyloctyloxy, 1,1-dimethylundecyloxy, 2-pentylnonyloxy, 1,2-dimethyltetradecyloxy, 1,1-dimethylpentadecyloxy and the like.

The term "$C_4$ to $C_{12}$ N, N-dialkylaminoalkyl" includes branched and straight chain alkyl groups which can be the same or different provided the total number of carbon atoms is not less than four nor more than twelve. As examples there can be named 2-dimethylaminoethyl, diethylaminomethyl, 3-dimethylaminopropyl, 1-dimethylamino-2-propyl, 3-diethylaminopropyl, 1-diethylamino-2-propyl, 2-dipropylaminoethyl, 2-di-i-propylaminoethyl, 3-dipropyl-aminopropyl, 3-dimethylaminopropyl, 4-diethylamino-n-butyl, 3-dibutylaminopropyl, 4-dimethylamino-n-butyl, 5-diethylaminopentyl, 5-dipropylaminopentyl, 6-dimethylamino-n-hexyl, 6-diethylamino-6-ethylhexyl, 4-dibutylamino-n-butyl, 8-dimethylamino-n-octyl, 8-diethylamino-n-octyl, 10-dimethylamino-n-decyl, 5-dipropylamino-2-pentyl and the like.

As used herein, the term "$C_2$ to $C_{18}$ alkenyl" means a monovalent aliphatic radical possessing a single double bond, for example, ethenyl (or vinyl), 2-propenyl (or allyl), 1-methyl-ethenyl (or isopropenyl), 2-methyl-2-propenyl, 2-methyl-1-propenyl, 2-butenyl, 3-butenyl, 1-pentenyl, 2-pentenyl, 3-methyl-2-butenyl, 2-methyl-1-butenyl (isoamylenyl), 3-methyl-1-butenyl, 1-hexenyl, 2-hexenyl, 3-hexenyl, 2-heptenyl, 1-octenyl, 1-hexadecenyl, 9-octadecenyl, 9-decenyl, 1-methyl-4-butenyl, 4-pentenyl, 1-ethyl-1-propenyl, 1-ethyl-3-propenyl, 10-undecenyl and the like.

Anhydrides of alkanoic acids of two to five carbon atoms include acetic anhydride, propionic anhydride, butyric anhydride, isobutyric anhydride, valeric anhydride, isovaleric anhydride, α-methylbutyric anhydride, pivalic anhydride and the like. Acetic anhydride is preferred because of its low cost and high reactivity, however the other above-named anhydrides are also satisfactory.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resins the compounds of Formula I develop an orange-red through green to a blackish-purple colored image of good to excellent tinctorial strength, and possessing excellent light stability, resistance to sublimation and xerographic copiability. The compounds are thus highly suitable for use as colorless precursors, that is color-forming substances in pressure-sensitive carbonless duplicating systems. The darker violets and bluish-black colors can be used alone as color formers to produce images which are readily copiable, whereas the reds, greens and blue colors can be used as toners in admixture with other color formers to produce images of a neutral shade which desirably are readily copiable by xerographic means. Moreover, the compounds of Formula I, in particular those wherein one of $R^1$ and $R^2$ represents

in which B represents -OY or

wherein Y is $C_2$ to $C_{18}$ alkyl, $C_2$ to $C_{18}$ alkenyl, benzyl or benzyl substituted in the benzene ring thereof by $C_1$ to $C_{12}$ alkyl, halo or $C_1$ to $C_8$ alkoxy; Y' is hydrogen or $C_1$ to $C_{18}$ alkyl; Y" is hydrogen, $C_1$ $C_{18}$ alkyl or $C_4$ to $C_{12}$ N,N-di-alkylaminoalkyl have enhanced solubility in common and inexpensive organic solvents such as odorless mineral spirits, kerosene, vegetable oils and the like; and those wherein one of $R^1$ and $R^2$ is an alkali-metal cation, an ammonium cation or a $C_1$ to $C_{18}$ mono-, di- or trialkylammonium cation salt of the carboxy group are soluble in water and lower-alkanols thereby avoiding the need for more expensive, specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such application is as follows. Solutions containing one or more colorlss precursor compounds of Formula I, optionally in admixture with other color formers, in suitable solvents are microencapsulated by well-known procedures for example as described in U.S. Pat. No. 3,649,649. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms orange-red to violet-black colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from orange-red to violet-black depending on the particular commpound of the invention employed. The ability of the compounds of Formula I to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The compounds of this invention which are soluble in water and lower-alkanols may be incorporated in any of the commercial hectographic or spirit-reproducing copying systems such as described in British Pat. No. 1,427,318 published Mar. 10, 1976. In such systems a transfer sheet coated on one side with a layer containing one or more water- or lower alkanol-soluble color formers of Formula I is placed with its coated surface against one surface of a master paper which is then typed, written or marked on, causing transfer of the coating as a substantially colorless reverse image to the master paper at the points where the transfer sheet and master paper have been pressed together. The master paper is then brought into contact with a succession of sheets of paper moistened with a suitable spirit-reproducing fluid such as ethanol. The fluid dissolves a part of the color former and transfers it to each paper sheet where it combines with an electron-accepting substance, to give a orangish-red to violet-black colored image which duplicates the original typing or writing on the master paper.

The best mode contemplated by the inventors of carrying out this invention will now be described so as to enable any person skilled in the art to which it pertains to make and use the same.

In accordance with one of the process aspects of this invention the 3-X-3-Z-4-$R^\circ$-5-$R^1$-6-$R^2$-7-$R^3$-phthalides of Formula I wherein $R^0$, $R^1$, $R^2$ and $R^3$ each represent hydrogen or halo or when $R^\circ$, $R^3$ and one of $R^1$ and $R^2$ are each hydrogen and the other represents nitro, dialkylamino or carboxy are obtained by interacting approximately an equimolar quantity of the appropriate 2-(X-carbonyl)-3-$R^\circ$-4-$R^1$-5-$R^2$-6-$R^3$-benzoic acid with the appropriate 3-$R^4$-N,N-(R)$_2$-aniline or a 1-$R^{6'}$-2-$R^{5'}$-5/6-$Y^{1'}$-indole. The reaction is conveniently carried out in the presence of an anhydride of an alkanoic acid having from 2 to 5 carbon atoms, for example, acetic anhydride at a temperature in the range of 10° to 140° C. for from approximately thirty minutes to eighteen hours. The 3-X-3-Z-4-$R^\circ$-5-$R^1$-6-$R^2$-7-$R^3$-phthalide thus obtained can be isolated by filtration if it is insoluble in the reaction medium or by dilution of the reaction medium with a miscible solvent in which the product is insoluble, for example, a lower-alkanol or low molecular weight hydrocarbon, for example, isopropyl alcohol or hexane to effect precipitation of the phthalide. Alternatively, the reaction mixture can be poured into an aqueous base or an aqueous base added to the reaction mixture, for example, dilute ammonium hydroxide, sodium hydroxide or sodium carbonate and the phthalide extracted with an organic solvent, for example, benzene or toluene followed by evaporation of the organic solvent leaving the product as a residue. The phthalide once isolated can be purified by conventional means such as trituration or recrystallization from a suitable solvent. In a second alternative method, the reaction mixture can be added to an aqueous acid, for example, dilute hydrochloric acid and the pH adjusted by the addition of a dilute alkali, for example, dilute aqueous ammonium hydroxide or an alkaline salt, for example, sodium acetate and the product filtered or extracted as described above.

The 3-[(1-$R^6$-2-$R^5$-5/6-$Y^1$)-3-indolyl]-3-[(1-$R^{6'}$-2-$R^{5'}$-5/6-$Y^{1'}$)-3-indolyl]-4-$R°$-5-$R^1$-6-$R^2$-7-$R^3$-phthalides of Formula VI in which the indole moieties are the same can be prepared by interacting trimellitic anhydride with approximately two molecular proportions of the appropriate 1-$R^6$-2-$R^5$-5/6-$Y^1$-indole. The reaction is conveniently carried out in the anhydride of an alkanoic acid having from two to five carbon atoms, for example acetic anhydride at a temperature in the range of 10° to 140° C., but more desirably, at a temperature in the range of 75° to 140° C. to obtain the desired 3-[(1-$R^6$-2-$R^5$-5/6-$Y^1$)-3-indolyl]-3-[(1-$R^{6'}$-2-$R^{5'}$-5/6-$Y^{1'}$)-3-indolyl]-5/6-carboxyphthalide. The phthalides are isolated in a manner similar to that indicated in the first mode of synthesis described above.

In accordance with a further process aspect of the present invention the 3-X-3-Z-5/6-aminophthalides of Formula I can be prepared by reducing the corresponding 3-X-3-Z-5/6-nitrophthalide. The reduction is conveniently carried out in an acidic medium, for example, hydrochloric acid using a metal salt reducing agent, for example, stannous chloride at a temperature in the range of 0° to 80° C., but more desirably, at a temperature in the range of 50°–80° C. The desired phthalide is collected by filtration and purified by conventional means for example recrystallization from a suitable solvent after an aqueous alkali extraction.

In accordance with a fourth of the process aspects of this invention, the 3-X-3-Z-5/6-acetamidophthalide according to Formula I can be conveniently obtained by interacting the appropriate 3-(X-carbonyl)-5/6-aminobenzoic acid with approximately an equimolar quantity of an appropriate 3-$R^4$-N,N-(R)$_2$-aniline or a 1-$R^{6'}$-2-$R^{5'}$-5/6-$Y^{1'}$-indole in the presence of at least two molecular proportions of acetic anhydride. The product is isolated by adding water and dilute alkali to the reaction mixture and the product extracted with an organic solvent, for example, benzene or toluene followed by evaporation of the organic solvent leaving the phthalide as a crystalline material.

The 3-X-3-Z-5/6-COOY-phthalides of Formula I in which Y is $C_2$ to $C_{18}$ alkyl, a $C_2$ to $C_{18}$ alkenyl, a benzyl or a benzyl substituted in the benzene ring thereof by $C_1$ to $C_{12}$ alkyl, halo or $C_1$ to $C_8$ alkoxy are obtained by interacting a 3-X-3-Z-5/6-COOH-phthalide with an appropriate alkylating agent, for example, dimethyl sulfate, diethyl sulfate, ethyl iodide, butyl bromide, allyl chloride, octyl bromide, hexadecyl bromide or benzyl bromide in an inert diluent, for example, acetone, N,N-dimethylformamide or hexamethylphosphoramide in the presence of an alkali metal salt, for example, sodium hydroxide, sodium carbonate, potassium hydroxide or potassium carbonate. The reaction is conveniently carried out at a temperature in the range of 10° to 100° C. for approximately one to three hours. The 3-X-3-Z-5/6-COOY-phthalide thus obtained is isolated by adding the reaction mixture to water with subsequent extraction into and subsequent isolation from an aromatic solvent, for example, benzene or toluene. The organic layer is separated, dried over a suitable drying agent, followed by evaporation of the organic solvent leaving the phthalide as a residue. The product once isolated can be purified by conventional means such as trituration or recrystallization from a suitable solvent.

In accordance with another process aspect of this invention the 3-X-3-Z-5/6-CONY'Y'''-phthalides of Formula I are obtained by amidating the corresponding 3-X-3-Z-5/6-COOH-phthalide or the appropriate corresponding 3-X-3-Z-5/6-COOY-phthalide with the appropriate Y'Y''NH amine, for example, 3-(di-n-butylamino)-propylamine. The reaction is conveniently carried out optionally in the presence of an inert diluent or in the absence of an inert diluent at a temperature in the range of 90° to 150° C. for approximately five hours. The phthalide thus obtained can be isolated by adding the reaction mixture to water and the product extracted with an organic solvent, for example, benzene or toluene. The organic layer is separated and evaporated or distilled in vacuum to leave the product as a residue or oil.

The 3-X-3-Z-5/6-COOY-phthalides wherein the Y is an alkali metal cation, an ammonium cation or a mono-, di- or tri-alkylammonium cation are obtained by interacting the appropriate 3-X-3-Z-5/6-COOH-phthalide with approximately an equimolar quantity of an appropriate alkali metal salt, for example, sodium hydroxide, potassium hydroxide or lithium hydroxide, ammonium hydroxide or an amine, for example, 1,1,3,3-tetramethylbutylamine. The reaction is conveniently carried out in an inert diluent, for example, acetone at a temperature in the range of 10° to 50° C. for approximately five minutes to one hour. The phthalide thus obtained is isolated by dilution of the reaction medium with a miscible solvent in which the product is insoluble, for example, low molecular weight hydrocarbons such as hexane in order to effect precipitation of the product. The phthalide once isolated can be purified by conventional means such as trituration or recrystallization from a suitable solvent.

Both the known and the novel 2-X-carbonyl-3-$R°$-4-$R^1$-5-$R^2$-6-$R^3$-benzoic acids of Formula VII are prepared in similar fashion, by interacting a 3-$R°$-4-$R^1$-5-$R^2$-6-$R^3$-phthalic anhydride with a 1-$R^6$-2-$R^5$-5/6-$Y^1$-indole, a 1-$R^7$-pyrrole, or a 9-$R^8$-carbazole wherein $R°$, $R^1$, $R^2$, $R^3$, $R^5$, $R^6$, $R^7$, $R^8$ and $Y^1$ each have the same meanings given in relation to Formula I usually in the presence of a Lewis acid, for example, aluminum chloride or zinc chloride, and with a diluent such as benzene, toluene, xylene, chlorobenzene, 1,2-dichloroethane or o-dichlorobenzene at a temperature of about 0° to 150° C. The reaction is conveniently carried out in toluene in the presence of aluminum chloride at about 0° to 25° C. Alternatively, the more reactive indoles can be interacted in the absence of a Lewis acid by simply heating the reactants together in an inert solvent at about 80° to 150° C. The 2-(X-carbonyl)-3-$R°$-4-$R^1$-5-$R^2$-6-$R^3$-benzoic acids in which Lewis acids are used in their preparation are isolated by adding water to the reaction mixture or the reaction mixture to water or dilute mineral acid, for example, hydrochloric acid and subsequently separating the organic layer. The product is extracted from the organic layer with a dilute aqueous alkali solution and precipitated by the addition of a mineral acid, for example, hydrochloric acid. The benzoic acid is collected by filtration and may be purified by conventional means but is generally dried and used as is. Alternatively, in the case where the more reactive indoles are utilized, it is preferable not to use a Lewis acid and the 2-(X-carbonyl)-3-$R°$-4-$R^1$-5-$R^2$-6-$R^3$-benzoic acids are obtained by cooling the reaction mixture to ambient temperature and collecting the product by filtration. The product once isolated can be purified by conventional means but preferably the benzoic acid is dried and used as is.

In accordance with one of the process aspects of this invention, the 2-(X-carbonyl)-5/6-aminobenzoic acids of Formula VII are obtained by reducing the corresponding 2-(X-carbonyl)-5/6-nitrobenzoic acid. The reduction is conveniently carried out in an acidic medium, for example, hydrochloric acid using a metal salt reducing agent, for example, stannous chloride at a temperature in the range of 0° to 80° C., but preferably at a temperature in the range of 50°–80° C. The desired benzoic acid is collected by filtration and purified if desired by conventional means but preferably it is dried and used as is.

It will, of course, be appreciated that reaction of an unsymmetrically substituted phthalic anhydride with an indole, pyrrole or carbazole can produce isomers or a mixture of isomers of 2-(heteroarylcarbonyl)benzoic acids. For example, reaction of a 4-substituteed phthalic anhydride with an indole, pyrrole or carbazole can produce either a 4- or 5-substituted 2-(heteroarylcarbonyl)benzoic acid or a mixture thereof. Similarly a 3-substituted phthalic anhydride can produce either a 3- or a 6-substituted 2-(heteroarylcarbonyl)benzoic acid or a mixture of these. These mixtures of isomeric 2-(heteroarylcarbonyl)benzoic acids can be separated by conventional means such as fractional crystallization or chromatography. Alternatively, the isomeric mixtures can be reacted directly with appropriate 3-$R^4$-N,N-(R)$_2$-anilines or 1-$R^{6'}$-2-$R^{5'}$-5/6-$Y^{1'}$-indoles to produce isomeric mixtures of phthalides of Formula I. Thus, reaction of a mixture of 4- and 5-substituted 2-(heteroarylcarbonyl)benzoic acids with a 3-$R^4$-N,N-(R)$_2$-aniline or a 1-$R^{6'}$-2-$R^{5'}$-5/6$Y^{1'}$-indole will produce a mixture of 5- and 6-substituted phthalides. The mixtures of phthalides can, if desired, be separated by conventional means or simply and preferably used as mixtures in the practice of this invention. Throughout this application where the possibility of different isomeric products being formed is present, the nomenclature 4/5, 5/6 and so forth is adopted meaning the product obtained or claimed is a mixture of the isomers.

Indole, the substituted indoles, pyrrole, the substituted pyrroles, carbazoles and the substituted carbazoles required as intermediates for the preparation of the carbonylbenzoic acid intermediates of Formulas VII, VIII and IX and for the final products of Formulas I, II, III, IV, V and VI form an old and well-known class of compounds which are readily obtained by conventional procedures well known in the art. The following compounds are exemplary of indoles, pyrroles and carbazoles useful in the practice of this invention.

Indole,
1-Methylindole,
2-Methylindole,
1,2-Dimethylindole,
1-Ethyl-2-methylindole,
2-Phenylindole,
1-Propyl-2-methylindole,
1-Benzyl-2-methylindole,
1-Butyl-2-methylindole,
1-Octyl-2-methylindole,
2-Ethyl-5-methylindole,
1-Benzyl-5-fluoroindole,
1-Methyl-6-nitroindole,
5-Methoxy-1-butylindole,
1-Allyl-2-methylindole,
1,2-Dimethyl-6-nitroindole,
1-(4-Chlorobenzyl)-2-methyl-5-nitroindole,
2-Ethylindole,
2-Ethyl-1-methylindole,
1-Isopropylindole,
2-Isopropylindole,
1-Methyl-5-bromo-6-nitroindole,
2,5,6-Trimethylindole,
1-Isobutyl-2-methylindole,
6-Bromo-2-methylindole,
1-Hexylindole,
1-(2,5-Dimethylbenzyl)-2-methylindole,
2-Propylindole,
6-Chloro-2-phenylindole,
1-(2-Ethylhexyl)-2-methylindole,
1-(2,6-Dichlorobenzyl)-2-methylindole,
1-Vinyl-2-methylindole,
2-Ethyl-6-methylindole,
6-Fluoro-1-benzylindole,
1-(4-Bromobenzyl)-2-isopropylindole,
1-(3-Chlorobenzyl)-2-ethylindole,
5-Chloro-1-benzylindole,
1-(2-Fluorobenzyl)-2-methylindole,
5-Iodo-1-(1-methylhexyl)indole,
5,6-Dimethoxyindole,
1-(2-Methylbenzyl)-2-methylindole,
5,6-Dichloro-2-phenylindole,
1-Isoamylindole,
1-[3-(2-Methyl)-1-propenyl]-2-methoxyindole,
Pyrrole,
N-Methylpyrrole,
N-Ethylpyrrole,
N-Propylpyrrole,
N-Isopropylpyrrole,
N-Phenylpyrrole,
Carbazole,
9-Methylcarbazole,
9-Ethylcarbazole,
9-Propylcarbazole,
9-Isopropylcarbazole, and
9-Phenylcarbazole.

The 3-$R^4$-N,N-(R)$_2$-anilines, which are required for interaction with the 2-(X-carbonyl)-3-$R^\circ$-4-$R^1$-5-$R^2$-6-$R^3$-benzoic acids of Formula VII to obtain the 3-X-3-[2-$R^4$-4-N(R)$_2$-phenyl]-4-$R^\circ$-5-$R^1$-6-$R^2$-7-$R^3$-phthalides of Formula II form an old and well-known class of compounds readily obtained by conventional procedures well known in the art. The following list of anilines exemplifies compounds falling within the ambit of the formula Z-H which are useful in the practice of the step in the processes of this invention for producing the aforesaid phthalides of Formula II.

N,N, N',N'-Tetramethyl-m-phenylenediamine,
N,N-Dibutylaniline,
N,N-Diethyl-3-ethoxyaniline,
N,N-Diethyl-m-anisidine,
N,N-Dimethylaniline,
N-Benzyl-N-ethylaniline,
N,N-Diethyl-m-toluidine,
N,N-Diethylaniline,
N-Ethyl-N-methylaniline,
N-Benzyl-N-methylaniline,
N-Benzyl-N-propylaniline,
N,N-Dimethyl-3-bromoaniline,
N,N,N',N'-Tetraisopropyl-m-phenylenediamine,
N,N-Dibutyl-3-fluoroaniline,
N,N-Diethyl-2-methoxy-3-chloroaniline, N-Benzyl-N-methyl-3-ethylaniline,
N,N,N',N'-Tetra-sec-butyl-m-phenylenediamine,
N-Benzyl-N-butyl-3-iodoaniline,
N,N-Diisopropyl-3-chloroaniline,
N-Benzyl-N-sec-butylaniline,
N,N-Di-sec-butylaniline,
N,N-Diethyl-3-isopropylaniline,
N,N-Diisobutylaniline,
N,N-Diethyl-2-propoxyaniline,
N,N-Dipropylaniline,
N-Isopropyl-N-methylaniline,
N-Methyl-N-propylaniline,
N,N,N',N'-Tetrabutyl-m-phenylenediamine,
N,N-Dipropyl-o-anisidine,
N-Isobutyl-N-ethylaniline,
N,N,N',N'-Tetraethyl-m-phenylenediamine,
N-Propyl-N-ethylaniline,
N,N-Diethyl-2-ethoxyaniline,
N-Benzyl-N-sec-butyl-2-propoxyaniline, and
N,N-Dimethyl-m-toluidine.

The molecular structures of the compounds of this invention were assigned on the basis of the modes of synthesis, elemental analysis and study of their infrared, nuclear magnetic resonance, and mass spectra.

The following examples will further illustrate the invention without, however, limiting it thereto.

EXAMPLE 1

A. To a stirred suspension of 22.5 g (0.15 mole) of phthalic anhydride and 61.0 g (0.30 mole) of 77.5 percent active 1-ethyl-2-methylindole in 120 ml of ethylene dichloride chilled to 0° to 5° C. by means of an ice bath, there was added in small portions 32.0 g (0.24 mole) of aluminum chloride. The mixture was maintained at 0°–5° C. for an additional 15 minutes, allowed to warm to room temperature and stirred overnight. Then, 240 ml of water was added to the reaction mixture and the ethylene dichloride layer was separated from the acidic aqueous layer. The organic layer was extracted with 600 ml of 3.5 percent aqueous sodium hydroxide. The alkaline extract was acidified with dilute hydrochloric acid and the separated solid collected, washed with water and dried to obtain 24.0 g of 2-[(1-ethyl-2-methyl-3-indolyl)carbonyl]benzoic acid (Formula VIII: $R°=R^1=R^2=R^3=Y^1=H$; $R^5=CH_3$; $R^6=CH_2CH_3$), a slightly pink solid having a melting point of 184°–185° C.

B. A mixture of 12.28 g (0.04 mole) of 2-[(1-ethyl-2-methyl3-indol)carbonyl]benzoic acid, prepared as described in part A above, 10.7 g (0.043 mole) of 90 percent active N,N,N',N'-tetraethyl-m-phenylenediamine and 6.0 ml of acetic anhydride was stirred at room temperature for seventeen hours. The reaction mixture was diluted with 26.0 ml of ethanol, stirred and filtered. The separated solid was washed with diethylether and dried to yield 11.8 g of 3-[2,4-bis(diethylamino)phenyl-]-3-(1-ethyl-2methyl-3-indolyl)phthalide (Formula III: $R°=R^1=R^2=R^3=Y^1=H$; $R=R^6=CH_2CH_3$; $R^4=N(CH_2CH_3)_2$; $R^5=CH_3$), a white crystalline material which melted at 139°–140° C. The infrared spectrum showed a significant band at 1760 cm$^{-1}$ (C=O; s) and the nuclear magnetic resonance spectrum was in accord with the structure. A solution of this product in benzene developed a deep blue-black color when spotted on silica gel.

C. In a procedure similar to that described above in part B of this example, 12.28 g (0.04 mole) of 2-[(1-ethyl-2-methyl-3-indolyl)carbonyl]benzoic acid, prepared as described in part A above, 8.57 g (0.05 mole) of N,N,N',N'-tetramethyl-m-phenylenediamine and 6.0 ml of acetic anhydride were interacted with stirring at room temperature overnight. The reaction mixture was then diluted with 13.0 ml of ethanol and the precipitate which separated was filtered and washed with 6.0 ml of ethanol. The filter cake was then reslurried in 30 ml of methanol, filtered and washed successively with methanol and diethylether. The material was dried in vacuo to obtain 15.8 g of 3-[2,4-bis(dimethylamino)phenyl]3-(1-ethyl-2-methyl-3-indolyl)phthalide (Formula III: $R°=R^1=R^2=R_3=Y^1=H$; $R=R^5=CH_3$; $R^4=N(CH_3)_2$; $R^6=CH_2CH_3$), a white crystalline solid which melted at 218°–222° C. The infrared spectrum was consistent with the structure. A benzene solution of the above product developed in intense grape-red color when streaked on a phenolic resin coated paper.

EXAMPLE 2

A. To a stirred suspension of 9.66 g (0.017 mole) of tetrachlorophthalic anhydride and 13.5 g (0.034 mole) of 80 percent active 1-ethyl-2-methylindole in 30 ml of benzene maintained at 0°–5° C. by means of a ice bath, 10.6 g (0.079 mole) of aluminum chloride was added in small increments. The reaction mixture was then maintained at 0° to 5° C. for an additional twenty minutes, allowed to warm to room temperature and stirred overnight. The mixture was transferred to a beaker and triturated successively with hexane, 10 percent hydrochloric acid, and lastly with 5 percent aqueous sodium hydroxide which had been heated to 70° C. The residual oil was filtered, acidified with dilute hydrochloric acid and allowed to stand overnight. On standing, the oil gave way to a solid which was collected by filtration, washed with water and dried to yield 6.8 g of 2-[(1-ethyl-2-methyl-3-indolyl)carbonyl]3,4,5,6-tetrachlorobenzoic acid (Formula VIII: $R°=R^1=R^2=R^3=Cl$; $R^5=CH_3$; $R^6=CH_3CH_2$; $Y^1=H$), an off white solid melting at 214°–216° C. Analysis by mass spectrum showed m/e peaks at 443 (M+, Cl=35) and 398 (M$^{30}$ —COOH).

B. A stirred mixture of 8.86 g of 2-[(1-ethyl-2-methyl-3-indolyl)carbonyl]-3,4,5,6-tetrachlorobenzoic acid, prepared as described in part A above, 4.0 g of N,N,N',N'-tetramethyl-m-phenylenediamine, and 10.0 ml of acetic anhydride was heated at reflux for a period of three hours. The reaction was then allowed to cool to room temperature, and the tan precipitate which formed was filtered an washed with isopropanol. The material thus obtained was dissolved in 500 ml of benzene and the resulting solution extracted with 70 ml of 10 percent aqueous sodium hydroxide. The benzene solution was filtered and evaporated to dryness at ambient temperature yielding 1.5 g of 3-[2,4-bis(dimethylamino)-phenyl]-3-(1-ethyl-2-methyl-3-indolyl)-4,5,6,7-tetrachlorophthalide (Formula III: $R°=R^1=R^2=R^3=Cl$; $R=R^5=CH_3$; $R^4=N(CH_3)_2$; $R^6=CH_2CH_3$; $Y^1=H$), a white solid which melted with decomposition at 227°–229° C. A significant infrared maximum occurred at 1770 cm$^{-1}$ (C=O; s). The nuclear magnetic resonance spectrum was in complete agreement with the assigned structure. A benzene solution of this product spotted on silica gel developed an intense purple color.

EXAMPLE 3

A. A solution of 67.2 g (0.4 mole) of 4-nitrophthalic anhydride and 63.0 g (0.32 mole) of 80.6 percent active 1-ethyl-2-methylindole in 50 ml of ethylene dichloride was heated at reflux for two hours. The reaction mixture was then allowed to cool to room temperature. The yellow precipitate which separated was collected by filtration, washed with fresh ethylene dichloride and dried to obtain 64.5 g of 2-[(1-ethyl-2-methyl-3-indolyl)-carbonyl]-5-nitrobenzoic acid (Formula VIII: $R^°=R^2=R^3=Y^1=H$; $R^1=NO_2$; $R^5=CH_3$; $R^6=CH_2CH_3$) having a meltingpoint of 203°–204° C.

B. A mixture of 3.68 g (0.01 mole) of 2-[(1-ethyl-2-methyl3-indolyl)carbonyl]-5-nitrobenzoic acid, prepared as described in part A above, and 2.0 g (0.012 mole) of N,N,N',N'-tetramethyl-m-phenylenediamine in 10.0 ml of acetic anhydride was heated at 90° C. for one hour and then allowed to cool to 25° C. The solid which separated was collected by filtration, washed with diethylether and dried to obtain 3.8 g of 3-[2,4-bis(-dimethylamino)phenyl]-3(1-ethyl-2-methyl-3-indolyl)-6-nitrophthalide (Formula III: $R^°=R^1=R^3=Y^1=H$; $R^2=NO_2$; $R=R^5=CH_3$; $R^4=N(CH_3)_2$; $R^6=CH_2CH_3$) as an orange solid which melted over the range 185°–187° C. The nuclear magnetic resonance spectrum was in accord with the assigned structure. A benzene solution of this product developed a black-purple color when spotted on silica gel.

C. A solution of 25.0 g (0.054 mole) of 3-[2,4-bis(-dimethylaamino)phenyl]-3-(1-ethyl-2-methyl-3-indolyl)-6-nitrophthalide, prepared as described in part B above, in 285 ml of concentrated hydrochloric acid was heated to 60° C. at which temperature 31.25 g (0.412 mole) of stannous chloride dihydrate was added at such a rate as to maintain the temperature at 60° C. After the addition was complete, the solution was heated to 70° C. and held there for a period of one hour and then allowed to cool to 25° C. The green-colored solid which separated was collected by filtration and was slurried in five percent aqueous sodium hydroxide solution. The resulting suspension was extracted with 500 ml of toluene at room temperature and the toluene extract was filtered, decolorized, and dried over sodium sulfate. On standing, a cream solid separated from the toluene solution. The solid was filtered off and dried to obtain 2.9 g of 3-[2,4-bis(dimethylamino)phenyl]-3-(1-ethyl2-methyl-3-indolyl)-6-aminophthalide (Formula III: $R^°=R^1=R^3=Y^1=H$; $R^2=NH_2$; $R=R^5=CH_3$; $R^4=N(CH_3)_2$; $R^6=CH_2CH_3$) having a melting point of 206°–209° C. Infrared analysis showed a maximum at 1727 cm$^{-1}$ (C=O; s). The nuclear magnetic resonance spectrum was concordant with the assigned structure. A toluene solution of the above compound developed an intense grape-black color when spotted on a paper coated with phenolic resin.

D. To a solution of 7.04 g (0.02 mole) of 2-[(1-ethyl-2-methyl-3-indolyl)carbonyl]-5-nitrobenzoic acid, prepared as described in part A of this example, in 70 ml of concentrated hydrochloric acid, there was added 13.5 g (0.06 mole) of stannous chloride dihydrate at such a rate as to allow the reaction to exotherm to 55° C. The temprature was maintained at 55° C. for an additional one-half hour. The reaction was then cooled to room temprature and the pH adjusted to six by the addition of 10 percent aqueous sodium hydroxide solution. The red precipitate thus formed was filtered off and extracted into acetone. The acetone solution was evaporated and the paste-like residue was slurried in diethylether and then the solid was collected by filtration to obtain 3.5 g of 2-[(1-ethyl-2-methyl-3-indolyl)-carbonyl]-5-aminobenzoic acid (Formula VIII: $R^3=R^2=R^°=Y^1=H$; $R^1=NH_2$; $R^5=CH_3$; $R^6=CH_2CH_3$), a red solid which melted at 187°–189° C.

E. A mixture of 3.22 g (0.01 mole) of 2-[(1-ethyl-2-methyl3-indolyl)carbonyl]-5-aminobenzoic acid, 118 g (0.01 mole) of N,N,N',N'-tetramethyl-m-phenylenediamine in 10.0 ml of acetic anhydride was heated to 50° C. for one-half hour. After cooling to ambient temperature, 50 ml of water was added and the reaction mixture was filtered. The filtrate was rendered alkaline with dilute aqueous sodium hydroxide in the presence of 100 ml of toluene. The toluene layer was separated, dried and evaporated to obtain as tan crystals 3-[2,4-bis(dimethylamino)phenyl]-3-(1-ethyl-2-methyl-3-indolyl)-6-acetamidophthalide (Formula III: $R^°=R^1=R^3=Y^1=H$; $R^2=NHCOCH_3$; $R=R^5=CH_3$; $R^4=N(CH_3)_2$; $R^6=CH_2CH_3$) having a melting point of 204°–206° C. Infrared analyses showed maxima at 1733 cm$^{-1}$ (C=O; s) and 1695 cm$^{-1}$ (C=O; s). Nuclear magnetic resonance analsis was consistent with the structure. An acetone solution of the above compound developed an intense grape color when spotted on silica gel.

EXAMPLE 4

A. Following the procedure described in part A of Example 1, 7.4 g (0.05 mole) of phthalic anhydride, 16.0 g (0.07 mole) of 79 percent active 1-n-butyl-2-methylindole and 13.3 g (0.01 mole) of aluminum chloride were interacted in 50 ml of benzene to obtain 2-[(1-n-butyl-2-methyl-3-indolyl)carbonyl]benzoic acid (Formula VIII: $R^°=R^1=R^2=R^3=Y^1=H$; $R^5=CH_3$; $R^6=(CH_2)_3CH_3$) a pale pink solid melting over the range 88°–92° C. The nuclear magnetic resonance spectrum was consistent with the structure. Infrared maxima were recorded at 1720 cm$^{-1}$ (C=O; s) and 1700 cm$^{-1}$ (C=O; s).

B. A mixture of 3.35 g (0.01 mole) of 2[(1-n-butyl-2-methyl-3-indolyl)carbonyl]benzoic acid, prepared as described in part A above, 1.80 g (0.011 mole) of N,N,N',N'-tetramethyl-m-phenylenediamine and five ml of acetic anhydride was stirred at ambient temperature for a period of approximately 18 hours The reaction mixture was then poured into a mixture of 40 ml of water, 40 ml of ligroin and 20 ml of 10 percent aqueous sodium hydroxide. The ligroin layer was separated and the white crystals which separated from the solution on standing, were collected by filtration and dried to obtain 3-[2,4-bis(dimethylamino)phenyl]-3-(1-n-butyl-2-methyl-3-indolyl)phthalide (Formula III: $R^°=R^1=R^2=R^3=Y^1=H$; $R=R^5=CH_3$; $R^4=N(CH_3)_2$; $R^6=(CH_2)_3CH_3$) which melted at 165°–167° C. A characteristic infrared maximum appeared at 1752 cm$^{-1}$ (C=O; s). A toluene solution of the product spotted on silica gel developed an intense purple-colored image.

C. In a manner similar to that described in part B above, 3.35 g (0.01 mole) of 2[(1-n-butyl-2-methyl-3-indolyl)carbonyl]-benzoic acid and 2.42 g (0.011 mole) of N,N,N',N'-tetraethyl-m-phenylenediamine were interacted to obtain 3-[2,4-bis(diethylamino)phenyl]-3-(1-n-butyl-2-methyl-3-indolyl)phthalide (Formula III: $R^°=R^1=R^2=R^3=Y^1=H$; $R=CH_2CH_3$; $R^4=N(CH_2CH_3)_2$; $R^5=CH_3$; $R^6=(CH_2)_3CH_3$), as tan-colored crystals which melted at 78°–80° C. A toluene solution of the product spotted on silica gel developed an intense blue-black-colored image.

EXAMPLE 5

A. In a manner similar to that described in part A of Example 1 hereinabove, 7.4 g (0.05 mole) of phthalic anhydride, 16.0 g (0.053 mole) of 76.5 percent active 1-n-octyl-2-methylindole, and 13.3 g (0.1 mole) of aluminum chloride were interacted in 50 ml of benzene to obtain 6.9 g of 2-[(1-n-octyl-2-methyl-3-indolyl)carbonyl]benzoic acid (Formula VIII: $R°=R^1=R^2=R^3=Y^1=H$; $R^5=CH_3$; $R^6=(CH_2)_7CH_3$), as a pink-colored powder which melted at 121°–123° C. The nuclear magnetic spectrum was in agreement with the structure and a significant maxima occurred at 1717 cm$^{-1}$ (C=O; s).

B. Proceeding in a manner similar to that described in part B of Example 4 above, 3.91 g (0.01 mole) of 2-[(1-n-octyl2-methyl-3-indolyl)carbonyl]benzoic acid, 1.80 g (0.011 mole) of N,N,N'N'-tetramethyl-m-phenylenediamine and five ml of acetic anhydride were interacted at ambient temprature for a period of approximately 24 hours to obtain, after recrystallization from methanol, 3-[2,4-bis(dimethylamino)phenyl]-3-(1-n-octyl-2-methyl-3-indolyl)phthalide (Formula III: $R°=R^1=R^2=R^3=Y^1=H$; $R=R^5=CH_3$; $R^4=N(CH_3)_2$; $R^6=(CH_2)_7CH_3$) which melted over the range 64°–68° C. A significant infrared absorption was observed at 1750 cm$^{-1}$ (C=O; s). Analysis by mass spectrum showed m/e peaks at 537 ($M^{30}$) and 493 ($M^+$—$CO_2$). A toluene solution of the product when spotted on a phenolic resin coated paper developed an intense grape-colored image.

EXAMPLE 6

A. Proceeding in a manner similar to that described in part A of Example 2, 14.3 g (0.05 mole) of tetrachlorophthalic anhydride, 16.0 g (0.07 mole) of 76 percent active 1-n-butyl-2-methylindole and 13.3 g (0.10 mole) of aluminum chloride were interacted in 100 ml of benzene. The reaction mixture was drowned in 200 ml of five percent hydrochloric acid with stirring. The solid which formed was collected by filtration, washed with water and dried to obtain 2-[(1-n-butyl-2-methyl3-indolyl)carbonyl]-3,4,5,6-tetrachlorobenzoic acid (Formula VIII: $R°=R^1=R^2=R^3=Y^1=H$; $R^5=CH_3$; $R^6=(CH_2)_3CH_3$), a pale yellow solid melting at 162°–164° C. The nuclear magnetic resonance spectrum was in accord with the structure.

B. A mixture of 5.20 g (0.01 mole) of 2-[(1-n-butyl-2-methyl-3-indolyl)carbonyl]-3,4,5,6-tetrachlorobenzoic acid, prepared as described in part A above, 2.0 g (0.012 mole) of N,N,N',N'-tetramethyl-m-phenylenediamine and five ml of acetic anhydride was warmed over a period of approximately forty minutes at 100° C. The reaction mixture was then cooled to ambient temperature, set aside overnight, rendered alkaline with 10 percent aqueous sodium hydroxide solution and extracted with benzene. Petroleum ether was slowly added to the separated benzene extract and the solid which slowly separated was collected by filtration and dried to obtain 3-[2,4-bis(dimethylamino)phenyl]-3-(1-n-butyl-2-methyl3-indolyl)-4,5,6,7-tetrachlorophthalide (Formula III: $R°=R^1=R^2=R^3=Cl$; $R=R^5=CH_3$; $R^4=N(CH_3)_2$; $R^6=(CH_2)_3CH_3$; $Y^1=H$), as white crystals having a melting point of 173°–175° C. The nuclear magnetic resonance spectrum was consistent with the structure; a maximum of 1770 cm$^{-1}$ (C=O; s) appeared in the infrared spectrum; the spectrum showed a m/e peak at 617 ($M^+$, 4 Cl).

EXAMPLE 7

A. Proceeding in the same manner as that described in part A of Example 6 above, 14.3 g (0.05 mole) of tetrachlorophthalic anhydride, 16.0 g (0.052 mole) of 76.5 percent active 1-n-octyl-2-methylindole and 13.3 g (0.10 mole) of aluminum chloride were interacted to obtain 2-[(1-n-octyl-2-methyl-3-indolyl)carbonyl[-3,4,5,6-tetrachlorobenzoic acid (Formula VIII: $R°=R^1=R^2=R^3=Cl$; $R^5=CH_3$; $R^6=(CH_2)_7CH_3$; $Y^1=H$), a pale orange solid melting at 132°–134° C. The infrared spectrum, showing a maximum at 1745 cm$^{-1}$ (C=O; s) and the nuclear magnetic resonance spectrum was in accord with the structure.

B. A mixture of 2.64 g (0.005 mole) of 2-[1-n-octyl-2-methyl-3-indolyl)carbonyl]-3,4,5,6-tetrachlorobenzoic acid, prepared as described in part A above, 1.0 g (0.006 mole) of N,N,N'N'-tetramethyl-m-phenylenediamine and three ml of acetic anhydride were interacted as described in Example 2, part C above to obtain 3-[2,4-bis(dimethylamino)phenyl]-3-(1-n-octyl-2-methyl3-indolyl)-4,5,6,7-tetrachlorphthalide (Formula III: $R°=R^1=R^2=R^3=Cl$; $R=CH_3$; $R^4=N(CH_3)_2$; $R^5=CH_3$; $R^6=(CH_2)_7CH_3$; $Y^1=H$), a pale yellow powder melting at 145°–147° C. The infrared spectrum showed a maximum appearing at 1770 cm$^{-1}$ (C=O; s) and the nuclear magnetic resonance spectrum was concordant with the structure.

EXAMPLE 8

A. A suspension of 14.8 g (0.10 mole) of phthalic anhydride, 10.5 g (0.05 mole) of 2-phenylindole and 82 ml of xylene was heated to 110° C. briefly, cooled to and maintained at 95° C. for approximately two hours. The solution was cooled to ambient temperature and the solid which separated was collected by filtration and dried to obtain 10.6 g of 2-[(2-phenyl-3-indolyl)-carbonyl]benzoic acid (Formula VIII: $R°=R^1=R^2=R^3=R^6=Y^1=H$; $R^5=C_6H_5$) which melted at 106°–107° C. and had a nuclear magnetic resonance spectrum consistent with the assigned structure.

B. A mixture of 4.82 g (0.014 mole) of the 2-[(2-phenyl3-indolyl)carbonyl]benzoic acid from part A above, 3.60 g (0.02 mole) of N,N,N',N'-tetramethyl-m-phenylenediamine, and five ml of acetic anhydride was slowly heated until a purple color formed and maintained at this temperature for approximately two hours. After cooling to room temperature, sufficient 3N hydrochloric acid was added to the mixture to effect solution and stirring was continued for approximately 1.5 hours The resulting solution was filtered and the pH adjusted to five by the addition of sodium acetate. The precipitate which separated from the solution was collected by filtration and dried to obtain 3-[2,4-bis(dimethylamino)phenyl[-3-(2-phenyl-3-indolyl)phthalide (Formula III: $R°=R^1=R^2=R^3=R^6=Y^1=H$; $R=CH_3$; $R^4=N(CH_3)_2$; $R^5=C_6H_5$9. After recrystalization from toluene and hexane, the off white-colored solid melted at 153°–155° C. Significant infrared maxima were observed at 3380 cm$^{-1}$ (NH; m) and 1750 cm$^{-1}$ (C=O; s). The nuclear magnetic resonance spectrum was consistent with the structure. A toluene solution of this product spotted on silica gel developed an intense grape-red-colored image.

EXAMPLE 9

A. Proceeding in a manner similar to part A of Example 8, but substituting 2-methylindole for 2-phenylindole, there was obtained 2-[(2-methyl-3-indolyl)carbonyl]benzoic acid (Formula VIII: $R°=R^1=R^2=R^3=R^6=Y^1=H$; $R^5=CH_3$), as pale pink-colored crystals melting at 198°–200° C.

B. A mixturwe of 8.37 g (0.03 mole) of 2-[(2-methyl-3-indolyl)carbonyl]benzoic acid, prepared as described in part A above, 8.37 g (0.05 mole) of N,N,N',N'-tetramethyl-m-phenylenediamine and 10 ml of acetic anhydride was interacted at 50° C. as described in part B of Example 8 above to obtain 3-[2,4-bis(dimethylamino)phenyl]-3-(2-methyl-3-indolyl)phthalide (Formula III: $R°=R^1=R^2=R^3=R^6=Y^1=H$; $R=R^5=CH_3$; $R^4=N(CH_3)_2$). After purification by slurrying in a benzene and ligroin mixture, the collected and dried product melted at 183°–186° C. The product had mass spectrum with a m/e peak at 425 (M+). Both the infrared and nuclear magnetic resonance spectra were consistent with this structure. A toluene solution of the product spotted on a phenolic resin coated paper developed an intense grape-colored image.

EXAMPLE 10

A. A mixture of 5.0 g (0.03 mole) of 5-methoxy-2-methylindole and 4.6 g (0.03 mole) of phthalic anhydride in 25 ml of ethylene dichloride was refluxed for ten hours, cooled to room temperature and the separated solid was collected by filtration and dried to obtain 2-[(2-methyl-5-methoxy-3-indolyl)carbonyl]benzoic acid (Formula VIII: $R°=R^1=R^2=R^3=R^6=H$; $R^5=CH_3$; $Y^1=OCH_3$), as a pale pink-colored solid which decomposed at 203°–204° C. The nuclear magnetic resonance and infrared spectra were consistent with the assigned structure.

B. A mixture of 2.0 g (0.006 mole) of 2-[(2-methyl-5-methoxy-3-indolyl)carbonyl]benzoic acid, obtained as described in part A above, 1.1 g (0.0067 mole) of N,N,N',N'-tetramethyl-m-phenylenediamine and six ml of acetic anhydride were interacted at 50°–55° C. in a manner similar to that described in Example 2, part B to obtain 2.5 g of 3-[2,4-bis(dimethylamino)-phenyl]-3-(2-methyl-5-methoxy-3-indolyl)phthalide (Formula III: $R°=R^1=R^2=R^3=R^6=H$; $R=R^5=CH_3$; $R^4=N(CH_3)_2$; $Y^1=OCH_3$), as a light pink-colored solid melting at 196°–198° C. with decomposition. The infrared spectrum, showing a significant maximum at 1740 cm$^{-1}$ (C=O; s) and the nuclear magnetic resonance spectrum were in accord with the structure. A toluene solution of this product spotted on a phenolic resin coated paper developed an intense violet-colored image.

EXAMPLE 11

A. A mixture of 5.0 g (0.034 mole) of phthalic anhydride and 5.0 g (0.034 mole of 2,5-dimethylindole in 30 ml of ethylene dichloride was refluxed for 20 hours, cooled and the separated solid filtered off and dried to obtain 3.8 g of 2-[(2,5-dimethyl-3-indolyl)carbonyl]benzoic acid (Formula VIII: $R°=R^1=R^2=R^3=R^6=H$; $R^5=CH_3$; $Y^1=CH_3$), as a pink-colored solid melting at 198°–200° C.

B. A mixture of 2.0 g (0.007 mole) of 2-[(2,5-dimethyl-3-indolyl)carbonyl]benzoic acid from part A above, 1.1 g (0.007 mole) of N,N,N',N'-tetramethyl-m-phenylenediamine and seven ml of acetic anhydride was interacted in a manner similar to that described in Example 3, part E above, to obtain 2.35 g of 3-[(2,4-bis(dimethylamino)phenyl]-3(2,5-dimethyl-3-indolyl)phthalide (Formula III: $R°=R^1=R^2=R^3=R^6=H$; $R=R^5=CH_3$; $R^4=N(CH_3)_2$; $Y^1=CH_3$), a light purple solid melting over the range of 100°–125° C. The infrared showed a characteristic absorpotion maximum at 1760 cm$^{-1}$ (C=O; s). A toluene solution of this product spotted on acid clay or phenolic resin developed an intense violet-colored image.

EXAMPLE 12

A mixture of 1.55 g (0.0036 mole) of 2-[(1,2-dimethyl-3-indolyl)carbonyl]-3,4,5,6-tetrabenzoic acid prepared in a manner similar to part A of Example 2, 0.58 g (0.0035 mole) of N,N,N',N'-tetramethyl-m-phenylenediamine and ten ml of acetic anhydride was heated to reflux for approximately one hour. After cooling to room temperature, the reaction mixture was poured into 20 ml of 10 percent hydrochloric acid and the mixture then rendered alkaline by the addition of concentrated ammonium hydroxide. The purple solid which separated was collected by filtration, dried, and crystallized twice from isopropyl acetate to obtain 3-[(2,4-bis(dimethylamino)phenyl]-3-(1,2-dimethyl-3-indolyl)-4,5,6,7-tetrachlorophthalide (Formula III: $R°=R^1=R^2=R^3=Cl$; $R=R^5=R^6=CH_3$; $R^4=N(CH_3)_2$; $Y^1=H$) which decomposed at 228°–229° C. The mass spectrum showed an m/e at 575 (M+, 4 Cl). A toluene solution of the product spotted on silica gel developed an intense purple-colored image.

EXAMPLE 13

A suspension of 1.36 g (0.01 mole) of m-amino-N,N-dimethylaniline in 20 of acetic anhydride was heated to 80°–90° C. for approximately thirty minutes and then cooled to room temperature. Three grams (0.01 mole) of 2-[(1-ethyl-2-methyl-3-indolyl)-carbonyl]benzoic acid, prepared as described in part A of Example 1, was added and the resulting mixture was heated at 60°–70° C. for approximately thirty minutes. After cooling, the reaction mixture was poured into 100 ml of 10 percent hydrochloric acid and the mixture made alkaline with 10 percent aqueous sodium hydroxide with the addition of ice. The solid which separated was collected by filtration and dried to obtain 3-[(2-acetamido-4-dimethylamino-phenyl]-3-(1-ethyl-2-methyl-3-indolyl)phthalide (Formula III: $R°=R^1=R^2=R^3=Y^1=H$;

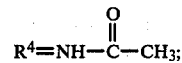

$R=R^5=CH_3$; $R^6=CH_2CH_3$) as a pale blue-colored solid melting over the range 180°–195° C. Infrared absorption maxima appeared at 1757 cm$^{-1}$ (C=O; s) and 1696 cm$^{-1}$ (C=O; s).

EXAMPLE 14

A mixture of 0.34 g (0.001 mole) of 2-[(1,2-dimethyl-3-indolyl)carbonyl]-5-dimethylaminobenzoic acid prepared as described in Example 1 of U.S. Pat. No. 3,540,910 was interacted with 0.16 g (0.001 mole) of N,N,N',N'-tetramethyl-m-phenylenediamine in 5 ml of acetic anhydried in a similar manner to the procedure described in Example 1, part C hereinabove to obtain 3-[2,4-bis(dimethylamino)phenyl]-3-(1,2-dimethyl-3-indolyl)-6-dimethylaminophthalide (Formula III:

$R^\circ=R^1=R^3=Y^1=H$; $R^2=N(CH_3)_2$; $R=R^5=R^6=CH_3$; $R^4=N(CH_3)_2$) which melts over the range of 146°–152° C. A significant infrared absorption maximum appeared at 1760 cm$^{-1}$ (C=O; s). A toluene solution of this product spotted on silica gel developed an intense grape-red-colored image.

EXAMPLE 15

A. To a mixture of 8.17 g (0.05 mole) of N-ethylcarbazole and 3.7 g (0.025 mole) of phthalic anhydride in 112 g of chlorobenzene, 6.65 g (0.05 mole) of aluminum chloride was added in small increments at ambient temperature after which the mixture was warmed in the range of 50°–70° C. for two hours. The reaction mixture was poured onto ice and rendered acidic by the addition of 10 percent hydrochloric acid. The chlorobenzene layer was separated and steam:distilled to remove the chlorobenzene. The residue was extracted with 10 percent agueous sodium hydroxide, filtered to remove the insolubles and then acidified with dilute hydrochloric acid. The solid which separated was collected by filtration, washed with water and dried to obtain 2-[(9-ethyl-3-carbazolyl)carbonyl]benzoic acid (Formula VII: $R^\circ=R^1=R^2=R^3=H$; $R^8=CH_2CH_3$) melting over the range 120°–130° C.

B. A mixture of 3.43 g (0.01 mole) of 2-[(9-ethyl-3-carbazolyl)carbonyl]benzoic acid, 1.80 g (0.011 mole) of N,N,N′,N′-tetramethyl-m-phenylenediamine and 4.0 ml of acetic anhydride was interacted in a manner similar to that described in Example 1, part C above to yield 3-[2,4-bis(dimethylamino)phenyl]-3-(9-ethyl-3-carbazolyl)pythalide (Formula V: $R^\circ=R^1=R^2=R^3=H$; $R=CH_3$; $R^4=N(CH_3)_2$; $R^8=CH_2CH_3$) which melted over the range 134°–142° C. A significant infrared absorption maximum appeared at 1753 cm$^{-1}$ (C=O; s). A toluene solution of this product spotted on silica gel developed a bordeaux-colored image.

EXAMPLE 16

A. To a mixture of 2.96 g (0.02 mole) of phthalic anhydride and 5.72 g (0.04 mole) of N-phenylpyrrole in 50 ml of chlorobenzene, maintained at 0°–5° C. in an ice bath, 810 g (0.06 mole) of aluminum chloride was added in small portions. The reaction mixture was held at 0°–5° C. for approximately two hours. The reaction was allowed to warm to room temperature and then set aside overnight at ambient temperature. The reaction mixture was worked up in a manner similar to that described in part A of Example 15 to obtain 2-[(1-phenyl-2-pyrrolyl)carbonyl]benzoic acid (Formula IX: $R^\circ=R^1=R^2=R^3=H$; $R^7=C_6H_5$) which melted over the range 159°–168° C.

B. A mixture of 2.91 g (0.01 mole) of 2-[(1-phenyl-2-pyrrolyl)carbonyl]benzoic acid prepared in part A above, 2.34 g (0.017 mole) of 84.6 percent active N,N,N′,N′-tetramethyl-m-phenylenediamine in 4.0 ml of acetic anhydride was interacted in a manner similar to that described in Example 1, part C to obtain 2.61 g of 3-[2,4-bis(dimethylamino)phenyl]-3-(1-phenyl-2-pyrrolyl)phthalide (Formula IV: $R^\circ=R^1=R^2=R^3=H$; $R=CH_3$; $R^4=N(CH_3)_2$; $R^7=C_6H_5$), a peach-colored powder melting at 193°–194° C. The infrared spectrum showed a maximum at 1760 cm$^{-1}$ (C=O; s). A toluene solution of this product spotted on silica gel developed an immediate orange-red-colored image.

EXAMPLE 17

A. Proceeding in a manner similar to that described in part A of Example 16, 14.8 g (0.1 mole) of phthalic anhydride, 16.2 g (0.2 mole) of N-methylpyrrole and 39.0 g (0.3 mole) of aluminum chloride were interacted in 50 ml of chlorobenzene to obtain 2-[(1-methyl-2-pyrrolyl)carbonyl]benzoic acid (Formula IX: $R^\circ=R^1=R^2=R^3=H$; $R^7=CH_3$) melting at 165°–167° C. A significant infrared absorption maximum appeared at 1710 cm$^{-1}$ (C=O; s).

B. A mixture of 4.58 g (0.02 mole) of 2-[(1-methyl-2-pyrrolyl)carbonyl]benzoic acid, from part A above, 3.61 g (0.022 mole) of N,N,N′,N′-tetramethyl-m-phenylenediamine and 3.0 ml of acetic anhydride was interacted in a manner similar to that described above in Example 1, part C to obtain 1.92 g of 3-[2,4-bis(dimethylamino)phenyl]-3-(1-methyl-2-pyrrolyl)phthalide (Formula IV: $R^\circ=R^1=R^2=R^3=H$; $R=R^7=CH_3$; $R^4=N(CH_3)_2$), a tan powder melting at 148°–150° C. A toluene solution of this product spotted on silica gel developed an intense red-colored image.

EXAMPLE 18

A. A stirred solution of 48.0 g (0.250 mole) of trimellitic anhydride and 45.0 g (0.314 mole) of 1-ethyl-2-methylindole in 350 ml of ethylene dichloride was heated at reflux for a period of approximately two hours, and then allowed to cool to ambient temperature. The solid, which separated, was collected by filtration, washed with 200 ml of ethylene dichloride and dried in vacuo at 60° C. to obtain 66.0 g of 4/5-carboxy-2-[(1-ethyl-2-methyl-3-indolyl)carbonyl]benzoic acid (Formula VIII: $R^1=R^2=H/COOH$; $R^\circ=R^3=Y^1=H$; $R^5=CH_3$; $R^6=CH_2CH_3$), a yellowish-orange solid melting over the range 198°–201° C. Infrared maxima appeared at 1730 (C=O; s) and 1700 cm$^{-1}$ (C=O; vs). The nuclear magnetic resonance spectrum was in agreement with the assigned structure.

B. A stirred mixture of 17.5 g (0.05 mole) of the 4/5-carboxy-2-[(1-ethyl-2-methyl-3-indolyl)carbonyl]benzoic acid, prepared as described in part A above, 8.5 g (0.052 mole) of N,N,N′,N′-tetramethyl-m-phenylenediamine and 25 ml of acetic anhydride was heated at 50° C. for a period of two hours and then allowed to cool to ambient temperature. After the addition of 25 ml of isopropyl alcohol, the resulting mixture was poured into water with vigorous stirring. The solid which separated was collected by filtration, washed with water and dried in vacuo at 60° C. to obtain 22.0 g of 3-[2,4-bis(dimethylamino)phenyl]-3-(1-ethyl-3-methyl-3-indolyl)-5/6-carboxyphthalide (Formula III: $R=R^5=CH_3$; $R^\circ=R^3=Y^1=H$; $R^1=R^2=H/COOH$; $R^4=N(CH_3)_2$; $R^6=CH_2CH_3$) as a dark purple solid melting over the range 149°–151° C. Infrared maxima appeared at 1775 (C=O; s) and 1720 cm$^{-1}$ (C=O; s).

C. Three milliliters of dimethyl sulfate was added to a refluxing mixture of 3.0 g of the 3-[2,4-bis(dimethylamino)phenyl]-3-(1-ethyl-2-methyl-3-indolyl)-5/6-carboxyphthalide prepared as described in part B above, 3.0 g of potassium carbonate and 100 ml of acetone. The reaction mixture was heated at reflux for a period of two hours and was then poured into water and the agueous mixture extracted with toluene. The toluene extract was washed successively with water and saturated salt solution and then evaporated to dryness. The residue was triturated with ligroin (b.p. 60°–90° C.) and the solid separated and dried to obtain 1.0 g of 3-[2,4-bis(dimethylamino)phenyl]-3-(1-ethyl-2-methyl-3-indolyl)-5/6-methoxycarbonylphthalide (Formula III: R=R$^5$=CH$_3$; R°=R$^3$=Y$^1$=H; R$^1$=R$^2$=H/COOCH$_3$; R$^4$=N(CH$_3$)$_2$; R$^6$αCH$_2$CH$_3$), a light purple solid melting over the range 72°–85° C. Infrared maxima appeared at 1760 (C=O; s) and 1730 cm$^{-1}$ (C=O; s). Analysis by mass spectrum showed m/e peaks at 511 (M$^+$) and at 452 (M$^+$—CO$_2$CH$_3$). A toluene solution of the produce spotted on silica gel, an acidic clay or a phenolic resin developed a grape-colored image.

EXAMPLE 19

To a stirred solution of 6.38 g (0.013 mole) of 3-[2,4-bis(dimethylamino)phenyl]-3-(1-ethyl-2-methyl-3-indolyl)-5/6-carboxyphthalide, prepared as described above in part B of Example 18, 150 ml of hexamethylphosphoramide and 10 ml of 25 percent aqueous sodium hydroxide, there was added 7.0 ml of ethyl iodide. The mixture was stirred at room temperature for a period of two hours. The reaction mixture was then drowned in water and the aqueous mixture was extracted with toluene. The toluene layer was washed with water, dried over anhydrous sodium sulfate, and evaporated. The residue was triturated with ligroin (b.p. 60°–90° C.) and the separated solid collected and dried to obtain 0.92 g of 3-[2,4-bis(dimethylamino)phenyl]-3-(1-ethyl-2-methyl-3-indolyl)-5/6-ethoxycarbonylphthalide (Formula III: R=R$^5$=CH$_3$; R°=R$^3$=Y$^1$=H; R$^1$=R$^2$=H/COOCH$_2$CH$_3$; R$^4$=N(CH$_3$)$_2$; R$^6$=CH$_2$CH$_3$), a light brown powder melting over the range 88°–97° C. Infrared maxima appeared at 1765 (C=O; s) and 1725 cm$^{-1}$ (C=O; s). The nuclear magnetic resonance spectrum was in agreement with the assigned structure. Analysis by mass spectrum showed m/e peak at 525 (M$^+$). A toluene solution of the product spotted on silica gel, an acidic clay or a phenolic resin developed a grape-colored image.

EXAMPLE 20

Following a procedure similar to that described above in part C of Example 18 but substituting dimethylformamide for acetone and n-octyl bromide for dimethyl sulfate, there was obtained 3-[2,4-bis(dimethylamino)phenyl]-3-(1-ethyl-2-methyl-3-indolyl)-5/6-n-octyloxycarbonylphthalide (Formula III: R=R$^5$=CH$_3$; R°=R$^3$=Y$^1$=H; R$^1$=R$^2$=H/COO(CH$_2$)$_7$CH$_3$; R$^4$=N(CH$_3$)$_2$; R$^6$=CH$_2$CH$_3$) as a light brown oil. Infrared maxima appeared at 1770 (C=O; s) and 1730 cm$^{-1}$ (C=O; s). A benzene solution of the product spotted on silica gel, an acidic clay or a phenolic resin developed a grape-colored image.

EXAMPLE 21

Following a procedure similar to that described above in Example 20 except that α-bromotoluene was used in place of n-octyl bromide, there was obtained 2.52 g of 3-[2,4-bis(dimethylamino)phenyl]-3-(1-ethyl-2-methyl-3-indolyl)-5/6-phenylmethoxy carbonylphthalide (Formula III: R=R$^5$=CH$_3$; R°=R$^3$=Y$^1$=H; R$^1$=R$^2$=H/COOCH$_2$C$_6$H$_5$; R$^4$=N(CH$_3$)$_2$; R$^6$=CH$_2$CH$_3$) a light purple powder melting over the range 72°–78° C. Infrared maxima appeared at 1770 cm$^{-1}$ (C=O; s). Analysis by mass spectrum showed m/e peaks at 587 (M$^+$) and 543 (M$^+$—CO$_2$). A tolune solution of the product spotted on silica gel, an acidic clay or a phenolic resin developed a grape-colored image.

EXAMPLE 22

A. A mixture of 35 g (0.10 mole) of 4/5-carboxy-2-[(1-ethyl-2-methyl-3-indolyl)carbonyl]benzoic acid prepared as described in Example 18, part A above, 20 g (0.103 mole) of N,N-diethyl-m-phenetidine and 60 ml of acetic anhydride was stirred at room temperature for a period of approximately eighteen hours. After the addition of 100 ml of isopropyl alcohol, the resulting mixture was poured into water with vigorous stirring. The solid which separated was collected by filtration, washed with water and dried to obtain 53.4 g of 3-(2-ethoxy-4-diethylaminophenyl)-3-(1-ethyl-2-methyl-3-indolyl)-5/6-carboxyphthalide (Formula III: R=R$^6$=C$_2$H$_5$; R°=R$^3$=Y$^1$=H; R$^1$=R$^2$=H/COOH; R$^4$=OC$_2$H$_5$; R$^5$=CH$_3$), a dark blue solid melting over the range of 130°–144° C. Infrared maxima appeared at 1765 (C=O; s) and 1725 cm$^{-1}$ (C=O; s). Analysis by mass spectrum showed m/e peaks at 526 (M$^+$) and 481 (M$^+$—CO$_2$H).

B. Employing a procedure similar to that described in part C of example 18, but interacting 5.0 g (0.0095 mole) of 3(2-ethoxy-4-diethylaminophenyl)-3-(1-ethyl-3-methyl-3-indolyl)-5/6-carboxyphthalide prepared as described in part A of this example with dimethyl sulfate instead of 3-[2,4-bis(dimethylamino)phenyl]-3-(1-ethyl-2-methyl-3-indolyl)-5/6-carboxyphthalide, there was obtained 4.9 g of 3-(2-ethoxy-4-diethylaminophenyl)-3-(1-ethyl-2-methyl-3-indolyl)-5/6-methoxycarbonylphthalide (Formula III: R=R$^6$=C$_2$H$_5$; R°=R$^3$=Y$^1$=H; R$^1$=R$^2$=H/COOCH$_3$; R$^4$=OC$_2$H$_5$; R$^5$=CH$_3$), a light green-colored solid melting over the range 96°–103° C. Infrared maxima appeared at 1765 (C=O; s) and 1730 cm$^{-1}$ (C=O; s). The nuclear magnetic resonance spectrum was in agreement with the assigned structure. Analysis by mass spectrum showed m/e peaks at 540 (M$^+$), 496 (M$^+$—CO$_2$) and 418 (M$^+$—COOCH$_3$). A toluene solution of the produce spotted on silica gel, an acidic clay or a phenolic resin developed a deep blue-colored image which had good lightfastness.

EXAMPLE 23

When diethyl sulfate was substituted for dimethyl sulfate for interaction with 3(2-ethoxy-4-diethylaminophenyl)-3-(1-ethyl-2-methyl-3-indolyl)-5/6-carboxyphthalide according to the procedure described in part B of Example 22, there was obtained 1.5 g of 3(2-ethoxy-4-diethylaminophenyl)-3-(1-ethyl-2-methyl-3-indolyl)-5/6-ethoxycarbonylphthalide (Formula III: R=R$^6$=C$_2$H$_5$; R°=R$^3$=Y$^1$=H; R$^1$=R$^2$=H/COOCH$_2$CH$_3$; R$^4$=OC$_2$H$_5$; R$^5$=(CH$_3$;), a light yellow solid melting over the range 141°–148° C. Infrared maxima appeared at 1750 (C=O; s) and 1732 cm$^{-1}$ (C=O; s). Analysis by mass spectrum showed m/e peaks at 554 (M$^+$), 510 (M$^+$—CO) and 481 (M$^+$—CO$_2$C$_2$H$_5$). A toluene solution of the product spotted on silica gel, an acidic clay or a phenolic resin developed a deep blue-colored image which had good lightfastness.

EXAMPLE 24

Following a procedure similar to that described above in Example 22, part B, 5.0 g (0.0095 mole) of 3-(2-ethoxy-4-diethylaminophenyl)-3-(1-ethyl-2-methyl-3-indolyl)-5/6-carboxyphthalide prepared as described in Example 22, part A was interacted with 2.0 g (0.0117 mole) of α-bromotoluene to obtain 3.4 g of 3-(2-ethoxy-4-diethylaminophenyl)-3-(1-ethyl-2-methyl-3-idolyl)-5/6-phenylmethoxycarbonylphthalide (Formula III: R=,R$^6$=C$_2$H$_5$; R$^°$=R$^3$=Y$^1$=H; R$^1$=R$^2$=H/COOCH$_2$C$_6$H$_5$; R$^4$=OC$_2$H$_5$; R$^5$=CH$_3$), a light yellow solid melting over the range 82–87° C. Infrared maxima appeared at 1765 (C=O; s) and 1725 cm$^{-1}$ (C=O; s). Analysis by mass spectrum showed m/e peaks at 616 (M$^+$) and 572 (M$^+$—CO$_2$). A toluene solution of the product spotted on silica gel, an acidic clay or a phenolic resin developed a deep blue-colored image which had good lightfastness.

EXAMPLE 25

When n-octyl bromide was substituted for α-bromotoluene for interaction with 3-(2-ethoxy-4-diethylaminophenyl)-3-(1-ethyl-2-methyl-3-indolyl)-5/6-carboxyphthalide according to the procedure described in Example 24, there was obtained 3-(2-ethyoxy-4-diethylaminophenyl)-3-(1-ethyl-2-methyl-3-indolyl)-5/6-n-octoxycarbonylphthalide (Formula III: R=R$^6$=C$_2$H$_5$; R$^°$=R$^3$=Y$^1$=H; R$^1$=R$^2$=H/COO-n-(CH$_2$)$_7$CH$_3$; R$^4$=OC$_2$H$_5$; R$^5$=CH$^3$), a light blue solid melting over the range 134°–162° C. A toluene solution of the product spotted on silica gel, an acidic clay or a phenolic resin developed a deep blue-colored image which had good lightfastness.

EXAMPLE 26

Substituting 1-bromohexadecane for n-octyl bromide for interaction with 3-(2-ethoxy-4-diethylaminophenyl)-3-(1-ethyl-2-methyl-3-indolyl)-5/6-carboxyphthalide according to the procedure described in Example 25, there was obtained 7.1 g of 3-(2-ethoxy-4-diethylaminophenyl)-3-(1-ethyl-2-methyl-3-indolyl)-5/6-hexadecanoxycarbonylphthalide (Formula III: R=R$^6$=C$_2$H$_5$; R$^°$=R$^3$=Y$^1$=H/COO(CH$_2$)$_{15}$CH$_3$; R$^4$=OC$_2$H$_5$; R$^5$=CH$_3$), a light brown oil. Infrared maxima appeared at 1765 (C=O; s) and 1725 cm$^{-1}$ (C=O; s). The nuclear magnetic resonance spectrum was in agreement with the assigned structure. Analysis by mass spectrum showed m/e peaks at 750 (M$^+$) and 706 (M$^+$—CO$_2$). A benzene solution of the product spotted on silica gel, an acidic clay or phenolic resin developed a deep blue-colored image which had good lightfastness.

EXAMPLE 27

To a stirred solution of 5.3 g of 3-(2-ethoxy-4-diethylaminophenyl)-3-(1-ethyl-2-methyl-3-indolyl)-5/6-carboxyphthalide prepared as described in Example 22, part A, in 25 ml of acetone there was added 2.6 of 1,1,3,3-tetramethylbutylamine. The mixture was stirred at ambient temperature for approximately ten minutes and then 160 ml of n-hexane was added. The supernatant liquid was decanted and the insoluble, brown, gummy residue triturated with n-hexane to obtain 6.2 g of the 1,1,3,3-tetramethylbutylammonium salt of 3-(2-ethoxy-4-diethylaminophenyl)-3-(1-ethyl-2-methyl-3-indolyl)-5/6-carboxyphthalide (Formula III: R$^°$=R$^3$=Y$^1$=H; R$^1$=R$^2$=H/CO$^\ominus$ON$^\oplus$H$_3$C(CH$_3$)$_2$CH$_2$C(CH$_3$)$_2$CH$_3$; R=R$^6$=C$_2$H$_5$; R$^4$=OC$_2$H$_5$; R$^5$=CH$_3$), a beige-colored solid melting over the range of 80°–105° C. with decomposition. Infrared spectral analysis showed significant maxima in the range from 2350 cm$^{-1}$ to 2150 cm$^{-1}$, and a strong absorption at 1760 cm$^{-1}$ (C=O; s). The assigned structure was corroborated by a concordant nuclear magnetic resonance spectrum. A toluene solution of the product spotted on silica gel, an acidic clay or a phenolic resin developed a deep blue-colored image which had good lightfastness. This product is also a water-soluble color-former.

EXAMPLE 28

A. Following a procedure similar to that described in part A of Example 22 but interacting, N,N-dimethylaniline instead of N,N-diethyl-m-phenetidine, with 4/5-carboxy-2-[(1-ethyl-2-methyl-3-indolyl)carbonyl]benzoic acid, there was obtained 3-(4-dimethylaminophenyl)-3-(1-ethyl-2-methyl-3-indolyl)-5/6-carboxyphthalide (Formula III: R=R$^5$=CH$_3$; R$^°$=R$^3$=R$^4$=Y$^1$=H; R$^1$=R$^2$=H/COOCH; R$^6$=C$_2$H$_5$), a blue-colored solid melting over the range 141°–160° C. Infrared maxima appeared at 1770 (C=O; s) and 1730 cm$^{-1}$ (C=O; s). Analysis by mass spectrum showed m/e peaks at 454 (M$^+$), 410 (M$^+$—CO$_2$) and 409 (M$^+$—COOH).

B. Employing a procedure similar to that described in part C of Example 18, but substituting 3-(4-dimethylaminophenyl)-3-(1-ethyl-2-methyl-3-indolyl)-5/6-carboxyphthalide prepared as described in part A above for 3-[2,4-bis(dimethylamino)phenyl]-3-(1-ethyl-2-methyl-3-indolyl)-5/6-carboxyphthalide for interaction with dimethyl sulfate, there was obtained 3-(4-dimethylaminophenyl)-3-(1-ethyl-2-methyl-3-indolyl)-5/6-methoxycarbonylphthalide (Formula III: R=R$^5$=CH$_3$; R$^°$=R$^3$=R$^4$=Y$^1$=H; R$^1$=R$^2$=H/COOCH$_3$; R$^6$=C$_2$H$_5$), a light yellow solid melting over the range 101°–110° C. Infrared maxima appeared at 1760 (C=O; s) and 1730 cm$^{-1}$ (C=O; s). The nuclear magnetic resonance spectrum was in agreement with the assigned structure. Analysis by mass spectrum showed m/e peaks at 468 (M$^+$), 424 (M$^+$—CO$_2$) and 409 (M$^+$—COOCH$_3$). A toluene solution of the product spotted on silica gel, an acidic clay or a phenolic resin developed a blue-colored image had good lightfastness.

EXAMPLE 29

Proceeding in a manner similar to that described above in Example 23, 3-(4-dimethylaminophenyl)-3-(1-ethyl-2-methyl-3-indolyl)-5/6-carboxyphthalide prepared as described in Example 28, part A, was interacted with diethyl sulfate to obtain 3-(4-dimethylaminophenyl)-3-(1-ethyl-2-methyl-3-indolyl)-5/6-ethoxy-carbonylphthalide (Formula III: R=R$^5$=CH$_3$; R$^°$=R$^3$=R$^4$=Y$^1$=H; R$^1$=R$^2$=H/COOC$_2$H$_5$; R$^6$=C$_2$H$_5$), a light green solid melting over the range 114°–131° C. Infrared maxima appeared at 1765 (C=O; s) and 1725 cm$^{-1}$ (C=O; s). Analysis by mass spectrum showed m/e peaks at 482 (M$^+$), 438 (M$^+$—CO$_2$) and 409 (M$^+$—$CO_2$C$_2$H$_5$). A toluene solution of the product spotted on silica gel, an acidic clay or a phenolic resin developed a blue-colored image which had good lightfastness.

EXAMPLE 30

When α-bromotoluene was substituted for diethyl sulfate in Example 29, there was obtained 3-(4-dimethylaminophenyl)-3-(1-ethyl-2-methyl-3-indolyl)-5/6-phenylmethoxycarbonylphthalide (Formula III: R=R$^5$=CH$_3$; R$^°$=R$^3$=R$^4$=Y$^1$=H; R$^1$=R$^2$=H/COOCH$_2$C$_6$H$_5$; R$^6$=C$_2$H$_5$), a light green-colored solid melting over the range 93°–98° C. Infrared maxima appeared at 1770 (C=O; s) and 1728 cm$^{-1}$ (C=O; s). Analysis by mass spectrum showed m/e peaks at 544 (M+) and 500 (M+—$CO_2$). A toluene solution of the product spotted on silica gel, an acidic clay or a phenolic resin developed a blue-colored image which had good lightfastness.

EXAMPLE 31

A. Following a procedure similar to that described in part A of Example 22, but using 15 g of N,N-diethylaniline instead of N,N-diethyl-m-phenetidine for interaction with 4/5-carboxy-2-](1-ethyl-2-methyl-3-indolyl)-carbonyl]benzoic acid, there was obtained 3-(4-diethylaminophenyl)-3-(1-ethyl-2-methyl-3-indolyl)-5/6-carboxyphthalide (Formula III: $R=R^6=C_2H_5$; $R°=R^3=R^4=Y^1=H$; $R^1=R^2=H/COOH$; $R^5=CH_3$), a blue solid melting over the range 169°-182° C. Infrared maxima appeared at 1765 (C=O; s) and 1730 cm$^{-1}$ (C=O; s). The nuclear magnetic resonsance spectrum was in agreement with the assigned structure.

B. Proceeding in a manner similar to that described in part C of Example 18, but using 3-(4-diethylaminophenyl)-3-(1-ethyl-2-methyl-3-indolyl)-5/6-carboxyphthalide prepared as described in part A above in place of 3-[2,4-bis(dimethylamino)phenyl]-3-(1-ethyl-2-methyl-3-indolyl)-5/6-carboxyphthalide for interaction with dimethyl sulfate, there was obtained 3-(4-diethylaminophenyl)-3-(1-ethyl-2-methyl-3-indolyl)-5/6methoxycarbonylphthalide (Formula III: $R=R^6=C_2H_5$; $R°=R^3=R^4=Y^1=H$; $R^1=R^2=H/COOCH_3$; $R^5=CH_3$), a light green solid melting over the range 114°-128° C. Infrared maxima appeared at 1765 (C=O; s) and 1730 cm$^{-1}$ C=O; s). A toluene solution of the product spotted on silica gel, an acidic clay or a phenolic resin developed a blue-colored image which had good lightfastness.

EXAMPLE 32

A. Employing a procedure similar to that described in part A of Example 22, but using m-chloro-N,N-dimethylaniline instead of N,N-diethyl-m-phenetidine for interaction with 4/5-carboxy-2-2-[(1-ethyl-2-methyl-3-indolyl)carbonyl]benzoic acid, there was obtained 3-(2-chloro-4-dimethylaminophenyl)-3-(1-ethyl-2-methyl-3-indolyl)-5/6-carboxyphthalide (Formula III: $R=R^5CH_3$; $R°=R^3=Y^1=H$; $R^1=R^2=H/COOH$; $R^4=Cl$; $R^6=C_2H_5$), as a greenish-blue solid melting over the range 130°-142° C. Infrared maxima appeared at 1770 (C=O; s) and 1725 cm$^{-1}$ (C=O; m).

B. Proceeding in a manner similar to that described in part C of Example 18, but using 3-(2-chloro-4-dimethylaminophenyl)-3-(1-ethyl-2-methyl-3-indolyl)-5/6carboxyphthalide prepared as described in part A above instead of 3-[2,4-bis(dimethylamino)phenyl]-3-(1-ethyl-2-methyl-3-indolyl)-5/6-carboxyphthalide for interaction with dimethyl sulfate, there was obtained 3-(2chloro-4-dimethyl-aminophenyl)-3-(1ethyl -2-methyl-3-indolyl)-5/6methoxycarbonyl-phthalide (Formula III: $R=R^5=CH_3$; $R°=R^3=Y^1=H$; $R^1=R^2=H/COOCH_3$; $R^4=Cl$; $R^6=C_2H_5$), as a light blue solid melting over the range 168°-193° C. Infrared maxima appeared at 1770 (C=O; s) and 1730 cm$^{-1}$ (C=O; s). A toluene solution of the product spotted on silica gel, an acidic clay or a phenolic resin developed a pale green-colored image.

EXAMPLE 33

A. Following a procedure similar to that described in part A of Example 22, but using N,N-m-diethyltoluidine instead of N,N-diethyl-m-phenetidine for interaction with 4/5-carboxy-2-[(1-ethyl-2-methyl-3-indolyl)carbonyl]benzoic acid, there was obtained 3-(2-methyl-4-diethylaminophenyl)-3-(1-ethyl-2-methyl-3-indolyl)-5/6-carboxyphthalide (Formula III: $R=R^6=C_2H_5$; $R°=R^3=Y^1=H$; $R^1=R^2=H/COOH$; $R^4=R^5=CH_3$), a turquoise-colored solid melting over the range 146°-162° C. Infrared maxima appeared at 1765 (C=O; s) and 1720 cm$^{-1}$ (C=O; s). Analysis by mass spectrum showed m/e peaks at 496 (M+), 452 (M+—$CO_2$) and 451 (M+—COOH).

B. Employing a procedure similar to that described in part C of Example 18, but using 2-(2-methyl-4-diethylaminophenyl)-3-(1-ethyl-2-methyl-3-indolyl)-5/6-carboxyphthalide prepared as described in part A above instead of 3-[2,4-bis(dimethylamino)-phenyl]-3-(1-ethyl-2-methyl-3-indolyl)-5/6-carboxyphthalide, there was obtained 3-(2-methyl-4-diethylaminophenyl)-3-(1-ethyl-2-methyl-3indolyl)-5/6-methoxycarbonylphthalide (Formula III: $R=R^6=C_2H_5$; $R°=R^3=Y^1=H$; $R^1=R^2=H/COOCH_3$; $R^4=R^5=CH_3$), a light yellow solid melting over the range 113°-120° C. Infrared maxima appeared at 1770 (C=O; s) and 1730 cm$^{-1}$ (C=O; s). The nuclear magnetic resonsance spectrum was in agreement with the assigned structure. Analysis by mass spectrum showed m/e peaks at 510 (M+) and 495 (M+—$COOCH_3$). A toluene solution of the product spotted on silica gel, an acidic clay or a phenolic resin developed a turquiose-colored image which had good lightfastness.

EXAMPLE 34

Proceeding in a manner similar to that described above in Example 23, 3-(2-methyl-4-diethylaminophenyl)-3-(1-ethyl-2-methyl-3-indolyl)-5/6-carboxyphthalide prepared as described in Example 33, part A was interacted with diethyl sulfate to obtain 3-(2-methyl-4-diethylaminophenyl)-3-(1-ethyl-2-methyl-3-indolyl)-5/6 -ethoxycarbonylphthalide (Formula III: $R=R^6=C_2H_5$; $R°=R^3=Y^1=H$; $R^1=R^2=H/COOCH_2H_5$; $R^4=R^5=CH_3$), a tan solid melting over the range 89°-144° C. Infrared maxima appeared at 1765 (C=O; s) and 1725 cm$^{-1}$ (C=O; s). Analysis by mass spectrum showed m/e peaks at 524 (M+), 480 (M+—$CO_2$) and 451 (M+—$CO_2C_2H_5$). A toluene solution of the product spotted on silica gel, an acidic clay or a phenolic resin developed a turquoise-colored image which had good lightfastness.

EXAMPLE 35

When α-bromotoluene was substituted for diethyl sulfate in Example 34 for interaction with 3-(2-methyl-4-diethylaminophenyl)-3-(1-ethyl-2-methyl-3-indolyl)-5/6-carboxyphthalide prepared as described in Example 33, part A, there was obtained 3-(2-methyl-4-diethylaminophenyl)-3-(1-ethyl-2-methyl-3-indolyl)-5/6-phenylmethoxycarbonylphthalide (Formula III: $R=R^6=C_2H_5$; $R°=R^3=Y^1=H$; $R^1=R^2=H/COOCH_2C_6H_5$; $R^4=R^5=CH_3$), a light yellow solid melting over the range 92°-98° C. Infrared maxima appeared at 1765 (C=O; s) and 1725 cm$^{-1}$ (C=O; s). Analysis by mass spectrum showed m/e peaks at 586 ($M^{30}$) and 542 (M+—$CO_2$). A toluene solution of the product spotted on silica gel, an acidic clay or a phenolic resin developed a turquoise-colored image having good lightfastness.

EXAMPLE 36

A. Following a procedure similar to that described in part A of Example 22, but using N,N-di-n-butylaniline instead of N,N-diethyl-m-phenetidine for interaction with 4/5-carboxy-2-[(1-ethyl-2-methyl-3-indolyl)carbonyl]benzoic acid, there was obtained 3-(4-di-n-butylaminophenyl)-3-(1-ethyl-2-methyl-3-indolyl)-5/6-carboxyphthalide (Formula III: $R=CH_2(CH_2)_2CH_3$; $R°=R^3=R^4=Y^1=H$; $R^1=R^2=H/COOH$; $R^5=CH_3$; $R^6=C_2H_5$), as a blue-colored solid melting over the range 81°–94° C. Infrared maxima appeared at 1760 ($C=O$; s) and 1725 cm$^{-1}$ ($C=O$; m).

B. Employing a procedure similar to that described in part C of Example 18 but using 3-(4-di-n-butylaminophenyl)-3-(1-ethyl-2-methyl-3-indolyl)-5/6-carboxyphthalide prepared as described in part A above instead of 3-[2,4-bis(dimethylamino)phenyl]-3-(1-ethyl-2-methyl-3-indolyl)-5/6-carboxyphthalide for interaction with dimethyl sulfate, there was obtained 3-(4-di-n-butylaminophenyl)-3-(1-ethyl2-methyl-3-indolyl)-5/6-methoxycarbonylphthalide (Formula III: $R=CH_2(CH_2)_2CH_3$; $R°=R^3=R^4=Y^1=H$; $R^1=R^2=H/COOCH_3$; $R^5=CH_3$; $R^6=C_2H_5$), a light yellow solid melting over the range 72°–94° C. Infrared maxima appeared at 1765 ($C=O$; s) and 1728 cm$^{-1}$ ($C=O$; s). Analysis by mass spectrum showed m/e peaks at 552 ($M^+$), 508 ($M^+-CO_2$) and 493 ($M^+-CO_2CH_3$). A toluene solution of the product spotted on silica gel, an acidic clay or a phenolic resin developed a blue-colored image which had good lightfastness.

EXAMPLE 37

A. Following a procedure similar to that described in part A of Example 22, but using N,N-dimethyl-m-anisidine instead of N,N-diethyl-m-phenetidine for interaction with 4/5carboxy-2-[(1ethyl-2-methyl-3-indolyl)-carbonyl]benzoic acid, there was obtained 3-(2-methoxy-4-dimethylaminophenyl)-3-(1-ethyl-2-methyl-3-indolyl)-5/6-carboxyphthalide (Formula III: $R=R^5=CH_3$; $R°=R^3=Y^1=H$; $R^1=R^2=H/COOH$; $R^4=OCH_3$; $R^6=C_2H_5$), a deep blue solid melting over the range 128°–133° C. Infrared maxima appeared at 1760 ($C=O$; s) and 1730 cm$^{-1}$ ($C=O$; m). Analysis by mass spectrum showed m/e peaks at 484 ($M^+$), 440 ($M^+-CO_2$) and 439 ($M^+-COOH$).

B. Employing a procedure similar to that described in part C of Example 18, but using 3-(2-methoxy-4-dimethylaminophenyl)-3-(1-ethyl-2-methyl-3-indolyl)-5/6-carboxyphthalide prepared as described in part A above instead of 3-[2,4-bis(dimethylamino)phenyl]-3-(1-ethyl-2-methyl-3-indolyl)-5/6carboxyphthalide for interaction with dimethyl sulfate, there was obtained 2-(2-methoxy-4-dimethylaminophenyl)-3-(1-ethyl-2-methyl-3-indolyl)-5/6-methoxycarbonylphthalide (Formula III: $R=R^5=CH_3$; $R°=R^3=Y^1=H$; $R^1=R^2=H/COOCH_3$; $R^4=OCH_3$; $R^6=C_2H_5$), as a light blue solid melting over the range 131°–135° C. Infrared maxima appeared at 1760 ($C=O$; s) and 1730 cm$^{-1}$ ($C=O$; s). Analysis by mass spectrum showed m/e peaks at 498 ($M^+$), 454 ($M^+-CO_2$) and 439 ($M^+-CO_2CH_3$). A toluene solution of the product spotted on silica gel, an acidic clay or a phenolic resin developed a deep blue-colored image which had good lightfastness.

EXAMPLE 38

A. Proceeding in a manner similar to that described in part A of Example 22, but using 3-n-butoxy-N,N-diethylaniline instead of N,N-diethyl-m-phenetidine for interaction with 4/5-carboxy-2-[(1-ethyl-2-methyl-3-indolyl)carbonyl]benzoic acid, there was obtained 3-(2-n-butoxy-4-diethylaminophenyl)-3-(1-ethyl-2-methyl-3-indolyl)-5/6-carboxyphthalide (Formula III: $R=R^6=C_2H_5$; $R°=R^3=Y^1=H$; $R^1=R^2=H/COOH$; $R^4OCH_2(CH_2)_2CH_3$; $R^5=CH_3$), a deep blue solid melting over the range 113°–125° C. Infrared maxima appeared at 1760 ($C=O$; s) and 1725 cm$^{-1}$ ($C=O$; m). Analysis by mass spectrum showed a m/e peak at 510 ($M+-CO_2$).

B. Following a procedure similar to that described in part C of Example 18, but using 3-(2-n-butoxy-4-diethylaminophenyl)-3-(1-ethyl-2-methyl-3-indolyl)-5/6-carboxyphthalide prepared as described in part A above instead of 3-[2,4-bis(dimethylamino)-phenyl]-3-(1-ethyl-2-methyl-3-indolyl)-5/6carboxyphthalide for interaction with dimethyl sulfate, there was obtained 3-(2-n-butoxyl-4-diethylaminophenyl)-3-(1-ethyl-2-methyl-3-indolyl)-5/6-methoxycarbonylphthalide (Formula III: $R=R^6=C_2H_5$; $R°=R^3=Y^1=H$; $R^1=R^2=H/COOCH_3$; $R^4OCH_2(CH_2)_2CH_3$; $R^5CH_3$), a light green oil. Infrared maxima appeared at 1765 ($C=O$; s) and 1730 cm$^{-1}$ ($C=O$; s). A toluene solution of the product spotted on silica gel, an acidic clay or a phenolic resin developed a deep blue-colored image which had good lightfastness.

EXAMPLE 39

A. A stirred mixture of 19.2 g (0.10 mole) of trimelitic anhydride, 35 g (0.22 mole) of 1-ethyl-2-methylindole and 75 ml of acetic anhydride was heated at reflux for approximately one hour, then cooled slightly below reflux after which there was slowly added 100 ml of methanol. The resulting solution was cooled to ambient temperature and slowly poured with stirring into a mixture of ice and water. The solid that formed was collected by filtration and dried in vacuo at 60° C. to obtain 3,3-bis(1-ethyl-2-methyl-3-indolyl)-5/6-carboxyphthalide (Formula VI: $R^1=R^2=H/COOH$; $R^5=R^{5'}=CH_3$; $R^6=R^{6'}=CH_2CH_3$; $R°=R^3=Y^1=Y^{1'}=H$), as a deep red solid melting over the range of 110°–119° C. Infrared maxima appeared at 1760 ($C=O$; s) and 1720 cm$^{-1}$ ($C=O$; m). The nuclear magnetic resonance spectrum was in accord with the assigned structure.

B. Following a procedure similar to that described above in part C of Example 18, but using 3,3-bis(1-ethyl-2-methyl-3-indolyl)-5/6-carboxyphthalide prepared as described above in part A of this example instead of 3-[2,4-bis(dimethylamino)phenyl]-3-(1-ethyl-2-methyl-3-indolyl)-5/6-carboxyphthalide for interaction with dimethyl sulfate, there was obtained 3,3-bis(1-ethyl-2-methyl-3-indolyl)-5/6-methoxycarbonylphthalide (Formula VI: $R^1=R^2=H/COOCH_3$; $R°=R^3=Y^1=Y^{1'}=H$; $R^5=R^{5'}=CH_3$; $R^6=R^{6'}=CH_2CH_3$), a tan solid melting over the range of 226°–229° C. with decomposition. Infrared maxima appeared at 1765 ($C=O$; s) and 1735 cm$^{-1}$ ($C=O$; s). The nuclear magnetic resonance spectrum was concordant with the assigned structure. Mass spectrum analysis showed m/e peaks at 506 ($M^+$), 462 ($M^+-CO_2$) and 447 ($M^+-CO_2CH_3$). An acetone solution of the product spotted on silica gel, an acidic clay or a phenolic resin developed a deep red-colored image which had good xerographic copiability and good lightfastness.

EXAMPLE 40

A stirred mixture of 3.0 g (0.006 mole) of 3,3-bis(1-ethyl-2-methyl-3-indolyl)-5/6-methoxycarbonylphthalide prepared as in Example 39, part B and 35 ml of 3-(di-n-butylamino)propylamine was heated at 125°–130° C. for approximately five hours and then allowed to cool to ambient temperature. The brown solution was poured into a mixture of water and toluene and the toluene layer was separated, washed with water and concentrated under reduced pressure. The excess amine was removed by vacuum distillation. There was thus obtained 3,3-bis(1-ethyl-2-methyl-3-indolyl)-5/6-(3-N,N-di-n-butylamino)propylaminocarbonylphthalide (Formula VI: $R^1=R^2=H/CONH(CH_2)_3N(n-C_4H_9)_2$; $R^5=R^{5'}=CH_3$; $R^6=R^{6'}=C_2H_5$; $R°=R^3=Y^1=Y^{1'}=H$), as a light brown oil. Infrared maxima appeared at 1770 (C=O; s and 1650 cm$^{-1}$ (C=O; s). The nuclear resonance spectrum was concordant with the assigned structure. When a soy oil solution of the product was spotted on silica gel, an acidic clay or a phenolic resin, a dark red-colored image developed which had good lightfastness.

EXAMPLE 41

A. Following a procedure similar to that described in Example 18, part B above, for interacting 10.6 g of 4/5-carboxy-2-[(1-ethyl-2-methyl-3-indolyl)carbonyl]-benzoic acid, prepared as described in Example 18, part A, and 7.0 g of 1-n-butyl-2-methylindole, there was obtained 16 g of 3-(1-ethyl-2-methyl-3-indolyl)-3-(1-n-butyl-2-methyl-3-indolyl)-5/6-carboxyphthalide (Formula VI: $R^1=R^2=H/COOH$; $R^5=R^{5'}=CH_3$; $R^6=C_2H_5$; $R^{6'}=n-C_4H_9$; $R°=R^3=Y^1=Y^{1'}=H$), a deep red solid melting over the range of 128°–138° C. with decomposition. Infrared maxima appeared at 1762 (C=O; s) and 1738 cm$^{-1}$ (C=O; s).

B. Employing a procedure similar to that described above in part B of Example 39, except that 3-(1-ethyl-2-methyl-3-indolyl)-3-(1-n-butyl-2-methyl-3-indolyl)-5/6-carboxyphthalide prepared as described above in part A of this example was used in place of 3,3-bis(1-ethyl-2-methyl-3-indolyl)-5/6-carboxyphthalide, there was obtained 3-(1-ethyl-2-methyl-3-indolyl)-3-(1-n-butyl-2-methyl-3-indolyl)-5/6-methoxycarbonylphthalide (Formula VI: $R^1=R^2=H/COOCH_3$; $R^5=R^{5'}=CH_3$; $R^6=C_2H_5$; $R^{6'}=n-C_4H_9$; $R°=R^3=Y^1=Y^{1'}=H$), a light orange solid melting over the range of 82°–94° C. Significant infrared maxima appeared at 1765 (C=O; s) and 1730 cm$^{-1}$ (C=O; s). Mass spectral analysis showed m/e peaks at 534 (M+) and 490 (M+—CO$_2$). A toluene solution of the product spotted on silica gel, an acidic clay or a phenolic resin developed a deep red-colored image which possessed good lightfastness.

EXAMPLE 42

A. Proceeding in a manner similar to that described in Example 41, part A above, but using 1-allyl-2-methylindole instead of 1-n-butyl-2-methylindole for interaction with 4/5-carboxy-2-[(1-ethyl-2-methyl-3-indolyl)carbonyl]benzoic acid, there was obtained 3-(1-ethyl-2-methyl-3-indolyl)-3-(1-allyl-2-methyl-3-indolyl)-5/6-carboxyphthalide (Formula VI: $R^1=R^2=H/COOH$; $R^5=R^{5'}=CH_3$; $R^6=C_2H_5$; $R^{6'}=CH_2-CH=CH_2$; $R°=R^3=Y^1=Y^{1'}=H$), a deep red solid melting at 135° C. with decomposition. Significant infrared maxima appeared at 1765 (C=O; s) and 1730 cm$^{-1}$ (C=O; m).

B. When 3-(1-ethyl-2-methyl-3-indolyl)-3-(1-allyl-2-methyl-3-indolyl)-5/6-carboxyphthalide prepared as described in part A of this example was substituted for 3,3-bis(1-ethyl-2-methyl-3-indolyl)-5/6-carboxyphthalide in the procedure described in part B of Example 39, there was obtained 3-(1-ethyl-2-methyl-3-indolyl)-3-(1-allyl-2-methyl-3-indolyl)-5/6-methoxycarbonylphthalide (Formula VI: $R^1=R^2=H/COOH$; $R^5=R^{5'}=CH_3$; $R^6=C_2H_5$; $R^{6'}=CH_2-CH=CH_2$; $R°=R^3=Y^1=Y^{1'}=H$), an orange solid melting over the range of 152°–164° C. Infrared spectral analysis showed maxima at 1760 (C=O; s) and 1732 cm$^{-1}$ (C=O; s). Nuclear magnetic resonance analysis was in accord with the assigned structure. Analysis by mass spectrum showed m/e peaks at 518 (M+), 474 (M+—CO$_2$) and 459 (M+—COOCH$_3$). A toluene solution of the product spotted on silica gel, and acid clay or a phenolic resin developed a deep red-colored image which had good lightfastness.

EXAMPLE 43

Employing a procedure similar to that described in Example 18, part B above, for interacting 4/5-carboxy-2-[(1-ethyl-2-methyl-3-indolyl)carbonyl]benzoic acid, prepared as described in Example 18, part A and 1-ethyl-2-methylindole, there was obtained 3,3-bis(1-ethyl-2-methyl-3-indolyl)-5/6-carboxyphthalide (Formula VI: $R^1=R^2=H/COOH$; $R^5=R^{5'}=CH_3$; $R^6=R^{6'}=CH_2CH_3$; $R°=R^3=Y^1=Y^{1'}=H$). Proceeding in a manner similar to that described in Example 39, part B, the following esters of the thus prepared 3,3-bis(1-ethyl-2-methyl-3-indolyl)-5/6-carboxyphthalide of Formula VI ($R°=R^3=Y^1=Y^{1'}=H$; $R^5=R^{5'}=CH_3$; $R^6=R^{6'}=CH_2CH_3$; $R^1/R^2=H/COOH$) above were prepared by esterification employing the appropriate dialkyl sulfate or organic halide. A toluene solution of these individual esters, when spotted on silica gel, an acidic clay or a phenolic resin, each developed a deep red-colored image which had good lightfastness. The infrared analyses, nuclear magnetic resonance analyses and mass spectral analyses obtained for the products of Examples 44 to 48 inclusive were concordant for the assigned structure given in those examples.

EXAMPLE 44

3,3-bis(1-ethyl-2-methyl-3-indolyl)-5/6-ethoxycarbonylphthalide (Formula VI: $R^1=R^2=H/COOC_2H_5$; $R^5=R^{5'}=CH_3$; $R^6=R^{6'}=CH_2CH_3$; $R°=R^3=Y^1=Y^{1'}=H$) was obtained as a pale yellow solid melting over the range of 176°–179° C.

EXAMPLE 45

3,3-Bis(1-ethyl-2-methyl-3-indolyl)-5/6-n-butoxycarbonylphthalide (Formula VI: $R^1=R^2=H/COO(CH_2)_3CH_3$; $R^5=R^{5'}=CH_3$; $R^6=R^{6'}=CH_2CH_3$; $R°=R^3=Y^1=Y^{1'}=H$) was obtained as a light orange solid melting at 88° C. with decomposition.

EXAMPLE 46

3,3-Bis(1-ethyl-2-methyl-3-indolyl)-5/6-n-octyloxycarbonylphthalide (Formula VI: $R^1=R^2=H/COO(CH_2)_7CH_3$; $R^5=R^{5'}=CH_3$; $R^6=R^{6'}=CH_2CH_3$; $R°=R^3=Y^1=Y^{1'}=H$) was obtained as an orange oil.

EXAMPLE 47

3,3-Bis(1-ethyl-2-methyl-3-indolyl)-5/6-phenylmethoxycarbonylphthalide (Formula VI: $R^1=R^2=H/COOCH_2C_6H_5$; $R^5=R^{5'}=CH_3$; $R^6=R^{6'}=CH_2CH_3$; $R°=R^3=Y^1=Y^{1'}=H$) was obtained as a light orange solid melting over the range of 94°–100° C. with decomposition.

EXAMPLE 48

3,3-Bis(1-ethyl-2-methyl-3-indolyl)-5/6-allyloxycarbonylphthalide (Formula VI: $R^1=R^2-H/COOCH_2CH=CH_2$; $R^5=R^{5'}=CH_3$; $R^6=R^{6'}=CH_2CH_3$; $R°=R^3=Y^1=Y^{1'}=H$) was obtained as a light orange solid melting over the range of 75°–87° C.

EXAMPLE 49

3,3-Bis(1-ethyl-2-methyl-3-indolyl)-5/6-n-hexadecyloxycarbonylphthalide (Formula VI: $R^1=R^2-H/COO(CH_2)_{15}CH_3$; $R^5=R^{5'}=CH_3$; $R^6=R^{6'}=CH_2CH_3$; $R°=R^3=Y^1=Y^{1'}=H$) was obtained as a dark red oil. Infrared maxima appeared at 1770 (C=O; s) and 1730 cm$^{-1}$ (C=O; s).

EXAMPLE 50

Proceeding in a manner similar to that described in Example 13 above, 4.43 g (0.01 mole) of 2-[(1-ethyl-2-methyl-3-indolyl)carbonyl]-3,4,5,6-tetrachlorobenzoic acid, prepared as described in Example 2, part A above, was interacted with 2.0 g (0.015 mole) of m-amino-N,N-dimethylaniline in the presence of ten ml of acetic anhydride to obtain 3-[2-acetamido-4-dimethylaminophenyl]-3-(1-ethyl-2-methyl-3-indolyl)-3,5,6,7-tetrachlorophthalide (Formula III: $R°=R^1=R^2=R^3=Cl$; $R=R^5=CH_3$;

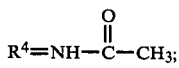

$R^6=CH_2CH_3$; $Y^1=H$) which developed a blue-green color when spotted on silica gel in the form of a toluene solution.

EXAMPLE 51

Following a procedure similar to that described in part B of Example 2 above, 4.45 g (0.01 mole) of 2-(1-ethyl-2-methyl-3-indolyl)carbonyl-3,4,5,6-tetrachlorobenzoic acid and 2.20 g (0.01 mole) of N,N,N',N'-tetraethyl-m-phenylenediamine were interacted in the presence of ten ml of acetic anhydride to obtain 3-[2,4-bis(diethylamino)phenyl]-3-(1-ethyl-2-methyl-3-indolyl)-4,5,6,7-tetrachlorophthalide (Formula III: $R°=R^1=R^2=R^3=Cl$; $R=R^6=CH_2CH_3$; $R^4=N(CH_2CH_3)_2$; $R^5=CH_3$; $Y^1=H$) melting at 100°–103° C. and showing a significant infrared absorption maxima at 1770 cm$^{-1}$ (C=O; s). A toluene solution of this compound developed an intense blue color when spotted on silica gel.

EXAMPLE 52

Employing a procedure similar to that described in part C of Example 1, 9.72 g (0.04 mole) of 2-(1,2-dimethyl-3-indolyl)-carbonylbenzoic acid prepared as described in U.S. Pat. No. 3,509,173, 8.57 g (0.05 mole) of N,N,N',N'-tetramethyl-m-phenylenediamine and 6.0 ml of acetic anhydride are interacted to obtain 3-[2,4-bis(-dimethylamino)phenyl]-3-(1,2-dimethyl-3-indolylphthalide (Formula III: $R°=R^1=R^2=R^3=Y^1=H$; $R=R^5=R^6=CH_3$; $R^4=N(CH_3)_2$).

EXAMPLE 53

A. Employing a procedure similar to that described in part A of Example 10 above, 7.15 g (0.025 mole) of tetrachlorophthalic anhydride and 3.65 g (0.028 mole) of 2-methylindole were interacted in 100 ml of ethylene dichloride to obtain 2-[(2-methyl-3-indolyl)carbonyl]-4,5,6,7-tetrachlorobenzoic acid (Formula VIII: $R°=R^1=R^2=R^3=Cl$; $R^5=CH_3$; $R^6=Y^1=H$), an orange solid melting at 200°–201° C.

B. A stirred mixture of 4.17 g of 2-[(2-methyl-3-indolyl)carbonyl-4,5,6,7-tetrachlorobenzoic acid, prepared as described in part A above and 3.28 g (0.02 mole) of N,N,N',N'-tetramethyl-m-phenylenediamine were interacted in the presence of 40 ml of acetic anhydride after the manner described in Example 2, part B above to obtain 3-[2,4-bis(dimethylamino)phenyl]-3-(2-methyl-3-indolyl)-4,5,6,7-tetrachlorophthalide (Formula III: $R°=R^1=R^2=R^3=Cl$; $R=R^5=CH_3$; $R^4=N(CH_3)_2$; $R^6=Y^1=H$) which showed an infrared carbonyl absorption maximum at 1775 cm$^{-1}$. A toluene solution of the compound developed a blue-black color when spotted on silica gel.

EXAMPLE 54

Proceeding in a manner similar to that described in part B of Example 5 above, 2.34 g (0.006 mole) of 2-[(1-n-octyl-2-methyl-3-indolyl)carbonyl]benzoic acid prepared according to Example 5, part A, and 2.40 g of N,N,N',N'-tetraethyl-m-phenylenediamine were interacted in the presence of 2.40 g of acetic anhydride to obtain 3-[2,4-bis(diethylamino)phenyl]-3-(1-n-octyl-2-methyl-3-indolyl)phthalide (Formula III: $R°=R^1=R^2=R^3=Y^1=H$; $R=CH_2CH_3$; $R^4=N(CH_2CH_3)_2$; $R^5=CH_3$; $R^6=(CH_2)_7CH_3$) as a tar-like semisolid. A toluene solution of this material developed as purple color when spotted on silica gel.

EXAMPLE 55

A. Proceeding in a manner similar to that described in part A of Example 10, 29.6 g (0.20 mole) of phthalic anhydride and 35.2 g (0.20 mole) of 5-nitro-2-methylindole were interacted in 100 ml of ethylene dichloride to obtain 2-[(2-methyl-5-nitro-3-indolyl)carbonyl]benzoic acid (Formula VIII: $R°=R^1=R^2=R^3=R^6=H$; $R^5=CH_3$; $Y^1=5-NO_2$), a red brown solid melting at 144°–148° C. and showing a strong carbonyl absorption maximum at 1700 cm$^{-1}$ in the infrared spectrum.

B. Following a procedure similar to that described in part B of Example 18 for interacting 3.24 g (0.01 mole) of 2-[(2-methyl-5-nitro-3-indolyl)carbonyl]benzoic acid, prepared as described in part A above, and 1.6 g (0.01 mole) of N,N,N',N'-tetramethyl-m-phenylenediamine in the presence of 5.0 ml of acetic anhydride, there is obtained 3-[2,4-bis(dimethylamino)phenyl]-3-(2-methyl-5-nitro-3-indolyl)phthalide (Formula III: $R°=R^1=R^2=R^3=R^6=H$; $R=R^5=CH_3$; $R^4=N(CH_3)_2$; $Y^1=NO_2$).

EXAMPLE 56

A. Using a procedure similar to the one described in part A of Example 18, 48.0 g (0.25 mole) of trimellitic anhydride and 32.8 g (0.25 mole) of 2-methylindole were interacted in 250 ml of ethylene dichloride to obtain 66.1 g of 4/5-carboxy-2-[(2-methyl-3-indolyl)carbonyl]benzoic acid (Formula VIII: $R^1=R^2=H/COOH$; $R°=R^3=R^6=Y^1=H$; $R^5=CH_3$) melting at 237°–241° C.

B. A procedure similar to that described in part B of Example 18 above, was followed for interacting 10 g (0.023 mole) of 4/5-carboxy-2-[(2-methyl-3-indolyl)carbonyl]benzoic acid, prepared as described in part A above, and 8.0 g (0.06 mole) of 2-methylindole in the presence of 50 ml of acetic anhydride. There was thus obtained 3,3-bis(2-methyl-3-indolyl)-5/6-carboxyphthalide (Formula VI: $R^1=R^2=H/COOH$; $R°=R^3=R^6=R^{6'}=Y^1=Y^{1'}=H$; $R^5=R^{5'}=CH_3$), a pink solid melting over the range of 145°–165° C.

EXAMPLE 57

A. Proceeding in a similar fashion to the one described in part A of Example 17, 28.6 g (0.01 mole) of tetrachlorophthalic anhydride, 16.2 g (0.2 mole) of N-methylpyrrole and 40 g (0.3 mole) of aluminum chloride were interacted in 50 ml of dry chlorobenzene to obtain 2-[(1-methyl-2-pyrrolyl)carbonyl]-3,4,5,6-tetrachlorobenzoic acid (Formula IX: $R°=R^1=R^2=R^3=Cl$; $R^7=CH_3$) having a melting point of 203°–205° C.

B. Employing the procedure of part B of Example 17 hereinabove, 3.70 g (0.01 mole) of 2-[(1-methyl-2-pyrrolyl)carbonyl]-3,4,5,6-tetrachlorobenzoic acid, prepared as described in part A above, and 2.0 g (0.012 mole) of N,N,N',N'-tetramethyl-m-phenylenediamine were interacted in the presence of 10 ml of acetic anhydride to obtain 3-[(2,4-bis(dimethylamino)phenyl]-3-(1-methyl-2-pyrrolyl)-4,5,6,7-tetrachlorophthalide (Formula IV: $R°=R^1=R^2=R^3=Cl$; $R=R^7=CH_3$; $R^4=N(CH_3)_2$).

EXAMPLE 58

To a stirred solution of 5.3 g of 3-(2-ethoxy-4-diethylaminophenyl)-3-(1-ethyl-2-methyl-3-indolyl)-5/6-carboxyphthalide, prepared as described in Example 22, part A, in 25 ml of acetone, there was added 30 ml of a 0.5 N methanolic sodium hydroxide solution. The mixture was stirred for approximately fifteen minutes at ambient temperature and concentrated to a syrup under vacuum. A small portion of fresh acetone was added to the syrup and the dark blue crystals which formed were collected by filtration. A small portion of hexane was added to the crystals resulting in a gummy residue. The residue was then triturated with more hexane to obtain a bright blue powder which was collected by filtration and dried to yield 4.8 g of the sodium salt of 3-(2-ethoxy-4-diethylaminophenyl)-3-(1-ethyl-2-methyl-3-indolyl)-5/6-carboxyphthalide (Formula III: $R°=R^3=Y^1=H$; $R^1=R^2=H/COO^{\ominus}Na^{\oplus}$; $R=R^6=C_2H_5$; $R^4=OC_2H_5$; $R^5=CH_3$), a bright blue colored powder melting over the range 82°–95° C. Infrared spectral analysis showed significant maxima at 1752 (C=O, s) and 1735 cm$^{-1}$ (C=O, s).

It is contemplated that by following procedures similar to those described in the foregoing examples but employing appropriate 2-{[(1-R$^6$-2-R$^5$-5/6-Y$^1$)-3-indolyl]carbonyl}-3-R°-4-R$^1$-5-R$^2$-6-R$^3$-benzoic acids of Formula VIII and appropriately substituted 3-R$^4$-N,N-(R)$_2$-anilines there will be obtained the 3-[2-R$^4$-4-N(R)$_2$-phenyl]3-[(1-R$^6$-2-R$^5$-5/6Y$^1$)-3-indolyl]-4-R°-5-R$^1$-6-R$^2$-7-R$^3$-phthalides of Formula III, Examples 59–75, presented in Table A hereinbelow.

TABLE A

| Ex. | R | R⁰ | R¹ | R² | R³ |
|---|---|---|---|---|---|
| 59 | n-C₄H₉ | H | H | N(C₂H₅)₂ | H |
| 60 | C₆H₅CH₂ | H | H/COONHC₈H₁₇ | H/COONHC₈H₁₇ | H |
| 61 | C₃H₇ | H | H | H | F |
| 62 | CH₃ | H | H/COO-i-C₃H₇ | H/COO-i-C₃H₇ | H |
| 63 | 4-Cl—C₆H₄CH₂ | H | H/COO⁻K⁺ | H/COO⁻K⁺ | H |
| 64 | i-C₃H₇ | H | I | H | H |
| 65 | CH₃ | H | Br | Br | H |
| 66 | 4-CH₃—C₆H₄CH₂ | H | H/COON(C₂H₅)₂ | H/COON(C₂H₅)₂ | H |
| 67 | i-C₄H₉ | Br | Br | Br | Br |
| 68 | 2-F—C₆H₄CH₂ | H | H/COO⁻NH₄⁺ | H/COO⁻NH₄⁺ | H |
| 69 | 2,5(CH₃)₂C₆H₃CH₂ | H | N(n-C₄H₉)₂ | H | H |
| 70 | C₂H₅ | H | H/COON(CH₂)₈—CH(CH₃)₂ | H/COON(CH₂)₈—CH(CH₃)₂ | H |
| 71 | C₆H₄CH₂ | H | H/COOCH₂C₆H₄Cl | H/COOCH₂C₆H₄Cl | H |
| 72 | CH₃ | H | H/COONC₆H₁₃ | H/COONC₆H₁₃ | H |
| 73 | n-C₄H₉ | H | H/COO⁻⁺NHCH₃C₁₄H₂₉ | H/COO⁻⁺NHCH₃C₁₄H₂₉ | H |
| 74 | C₂H₅ | H | H/COOCH₂C₆H₃—(CH₃)₂ | H/COOCH₂C₆H₃—(CH₃)₂ | H |
| 75 | C₆H₅CH₂, CH₃ | H | H/COONHC₂H₄N(CH₃)₂ | H/COONHC₂H₄N(CH₃)₂ | H |

| Ex. | R⁴ | R⁵ | R⁶ | Y¹ |
|---|---|---|---|---|
| 59 | N(n-C₄H₉)₂ | C₂H₅ | H | 5-CH₃ |
| 60 | OC₃H₇ | H | C₆H₅CH₂ | 5-F |
| 61 | N(C₃H₇)₂ | H | CH₃ | 6-NO₂ |
| 62 | Cl | C₂H₅ | H | 5,6-Cl₂ |
| 63 | C₃H₇ | CH₃ | 2-CH₃-1-C₃H₄ | H |
| 64 | N(i-C₃H₇) | CH₃ | 2,6-(Cl)₂C₆H₃CH₂ | H |
| 65 | N(CH₃)₂ | H | H | 5,6(OCH₃)₂ |
| 66 | OC₄H₉ | H | i-C₅H₁₁ | H |
| 67 | N(i-C₄H₉)₂ | CH₃ | C₂H₃ | H |
| 68 | Br | C₂H₅ | H | 5-CH₃ |
| 69 | NHCOCH₃ | H | 1-CH₃C₆H₁₂ | 5-I |
| 70 | OCH₃ | C₃H₇ | H | H |
| 71 | I | CH₃ | H | 5,6(CH₃)₂ |
| 72 | O-i-C₃H₇ | CH₃ | H | 6-Br |
| 73 | C₂H₅ | CH₃ | 2-F-C₆H₄CH₂ | H |
| 74 | OC₄H₉ | H | CH₃ | 5-Br-6-NO₂ |

TABLE A-continued

| | Phthalides of Formula III | | | |
|---|---|---|---|---|
| 75 | $C_2H_5$ | $CH_3$ | $C_2H_5$ | H |

It is contemplated that by following procedures similar to those described in the foregoing examples but employing the appropriate 2-(1-$R^7$-2-pyrrolyl)carbonyl-3-$R^\circ$-4-$R^1$-5-$R^2$-6-$R^3$-benzoic acids of Formula IX and appropriately substituted 3-$R^4$-N,N-(R)$_2$-anilines there will be obtained the 3-[2-$R^4$-4-N(R)$_2$-phenyl]-3-(1-$R^7$-2-pyrrolyl)-4-$R^\circ$-5-$R^1$-6-$R^2$-7-$R^3$-phthalides of Formula IV, Examples 76–87, presented in Table B hereinbelow.

bazolyl)-4-$R^\circ$-5-$R^1$-6-$R^2$-7-$R^3$-phthalides of Formula V, Examples 88–98, presented in Table C hereinbelow.

TABLE C

| | | | Phthalides of Formula V | | | | |
|---|---|---|---|---|---|---|---|
| Ex. | R | $R^0$ | $R^1$ | $R^2$ | $R^3$ | $R^4$ | $R^8$ |
| 88 | $C_6H_5CH_2$ | H | H/COOH | H/COOH | H | Cl | i-$C_3H_7$ |
| 89 | n-$C_3H_7$ | Cl | Cl | H | Cl | N(n-$C_3H_7$)$_2$ | $C_6H_5$ |
| 90 | $C_6H_5CH_2,C_2H_5$ | H | H/COO-n-$C_4H_9$ | H/COO-n-$C_4H_9$ | H | H | $C_2H_5$ |
| 91 | 3-Cl—$C_6H_4CH_2$ | H | H/COO$^\ominus$Na$^\oplus$ | H/COO$^\ominus$Na$^\oplus$ | H | I | n-$C_3H_7$ |
| 92 | i-$C_4H_9$ | H | H/COONHC$_{16}$H$_{33}$ | H/COONHC$_{16}$H$_{33}$ | H | NHCOCH$_3$ | CH$_3$ |
| 93 | $C_2H_5$ | Br | Br | Br | Br | N($C_2H_5$)$_2$ | i-$C_3H_7$ |
| 94 | 2,5-(CH$_3$)$_2$C$_6$H$_3$CH$_2$ | H | H/COOC$_2H_3$ | H/COOC$_2H_3$ | H | o-i-$C_3H_7$ | $C_2H_5$ |
| 95 | 2-F—$C_6H_4CH_2$ | H | H/COO$^\ominus\oplus$NH$_3C_6H_{13}$ | H/COO$^\ominus\oplus$NH$_3C_6H_{13}$ | H | Br | $C_2H_5$ |
| 96 | 2,6-Cl$_2$C$_6$H$_3$CH$_2$ | H | H/COON(C$_{18}$H$_{37}$)$_2$ | H/COON(C$_{18}$H$_{37}$)$_2$ | H | $C_3H_7$ | i-$C_3H_7$ |
| 97 | 4-Cl—$C_6H_8CH_2$ | H | H/COOC$_{12}$H$_{25}$ | H/COOC$_{12}$H$_{25}$ | H | Cl | CH$_3$ |
| 98 | n-$C_3H_7$ | H | H/COONHC$_3$H$_7$N(CH$_3$)$_2$ | H/COONHC$_3$H$_7$N(CH$_3$)$_2$ | H | CH$_3$ | $C_6H_5$ |

It is contemplated that by following procedures similar to those described in the foregoing examples but employing the appropriate 2-{[(1-$R^6$-2-$R^5$-5/6-$Y^1$)-3-indolyl[carbonyl]-3-$R^\circ$-4-$R^1$-5-$R^2$-6-$R^3$-benzoic acids of Formula VIII and appropriately substituted 1-$R^{6'}$-2-$R^{5'}$-5/6-$Y^{1'}$-indoles there will be obtained the 3-[(1-$R^6$-2-$R^5$-5/6-$Y^1$)-3-indolyl]-3-[(1-$R^{6'}$-2-$R^{5'}$-5/6-

TABLE B

| | | | Phthalides of Formula IV | | | | |
|---|---|---|---|---|---|---|---|
| Ex. | R | $R^0$ | $R^1$ | $R^2$ | $R^3$ | $R^4$ | $R^7$ |
| 76 | n-$C_4H_9$ | H | H | N($C_2H_5$)$_2$ | H | N(n-$C_4H_9$)$_2$ | $C_6H_5$ |
| 77 | 2,4-Cl$_2$—$C_6H_3CH_2$ | H | H/COO$^\ominus$Li$^\oplus$ | H/COO$^\ominus$Li$^\oplus$ | H | OC$_4H_9$ | $C_2H_5$ |
| 78 | $C_2H_5$ | H | Br | H | H | N($C_2H_5$)$_2$ | i-$C_3H_7$ |
| 79 | i-$C_3H_7$ | Br | Br | Br | Br | N(i-$C_3H_7$)$_2$ | $C_2H_5$ |
| 80 | 4-BrC$_6H_4CH_2$ | H | H/COOC$_{10}$H$_{21}$ | H/COOC$_{10}$H$_{21}$ | H | Cl | CH$_3$ |
| 81 | 2-F-$C_6H_4CH_2$ | H | H/COONHC$_{12}$H$_{23}$ | H/COONHC$_{12}$H$_{23}$ | H | OCH$_3$ | n-$C_3H_7$ |
| 82 | 2,5-(CH$_3$)$_2$C$_6H_3CH_2$ | H | H/COON(n-$C_4H_9$)$_2$ | H/COON(n-$C_4H_9$)$_2$ | H | I | $C_6H_5$ |
| 83 | $C_6H_5CH_2$, s-$C_4H_9$ | H | H/COO$^\ominus\oplus$NH$_3C_{18}H_{37}$ | H/COO$^\ominus\oplus$NH$_3C_{18}H_{37}$ | H | $C_3H_7$ | $C_2H_5$ |
| 84 | $C_2H_5$ | Cl | Cl | Cl | Cl | N($C_2H_5$)$_2$ | i-$C_3H_7$ |
| 85 | $C_6H_4CH_2$ | H | NO$_2$ | H | H | NHCOCH$_3$ | $C_6H_5$ |
| 86 | n-$C_3H_7$ | H | NHCOCH$_3$ | H | H | Br | $C_2H_5$ |
| 87 | CH$_3$ | H | H/COONHC$_2H_4$—N(i-$C_3H_7$)$_2$ | H/COONHC$_2H_4$—N(i-$C_3H_7$)$_2$ | H | CH$_3$ | CH$_3$ |

It is contemplated that by following procedures similar to those described in the foregoing examples but employing the appropriate 2-(9-$R^8$-3-carbazolyl)carbo-nyl-3-$R^\circ$-4-$R^1$-5-$R^2$-6-$R^3$-benzoic acids and appropriately substituted 3-$R^4$-N,N-(R)$_2$-anilines there will be obtained the 3-[2-$R^4$-4-N(R)$_2$-phenyl]-3-(9-$R^8$-3-car- $Y^{1'}$)-3-indolyl[-4-$R^\circ$-5-$R^1$-6-$R^2$-7-$R^3$-phthalides of Formula VI, Examples 99–112, presented in the Table D hereinbelow.

TABLE D

| | | | Phthalides of Formula VI | | | | | |
|---|---|---|---|---|---|---|---|---|
| Ex. | $R^o$ | $R^1/R^2$ | $R^3$ | $R^5$ | $R^6$ | $Y^1$ | $R^{5'}$ | $R^{6'}$ | $Y^{1'}$ |
| 99 | H | H/COO$^\ominus$K$^\oplus$ | H | H | H | H | H | $C_4H_9$ | OCH$_3$ |
| 100 | H | H/COOC$_{18}$H$_{37}$ | H | H | $C_6H_4CH_2$ | 5-F | $C_6H_5$ | H | H |
| 101 | H | H/COONHC$_6H_{13}$ | H | H | CH$_3$ | 6-NO$_2$ | $C_2H_5$ | H | CH$_3$ |
| 102 | H | H/COO$^\ominus\oplus$NH(CH$_3$)$_3$ | H | i-$C_3H_7$ | H | H | H | CH$_3$ | 5-Br,6-NO$_2$ |
| 103 | H | H/COONH$_2$ | H | CH$_3$ | H | 6-Br | CH$_3$ | 2,5-(CH$_3$)$_2$C$_6H_3CH_2$ | H |
| 104 | H | H/COOC$_{14}$H$_{29}$ | H | CH$_3$ | 2-($C_2H_5$)$C_6H_{12}$ | H | CH$_3$ | $C_2H_3$ | H |
| 105 | H | H/COON(CH$_3$)$_2$ | H | i-$C_3H_7$ | 4-BrC$_6H_4CH_2$ | H | $C_6H_5$ | H | 5,6-(CH$_3$)$_2$ |
| 106 | H | H/COO(CH$_2$)$_8$CH(CH$_3$)$_2$ | H | H | i-$C_5H_{11}$ | H | $C_6H_5$ | H | 5,6-(Cl)$_2$ |
| 107 | H | H/COO$^\ominus$NH$_4$ | H | CH$_3$ | 2-CH$_3$—$C_6H_4CH_2$ | H | H | 1-CH$_3$-$C_6H_{12}$ | 5-I |
| 108 | H | H/COOCH$_2C_6H_4Cl$ | H | CH$_3$ | 3-(2-CH$_3$)-1-$C_3H_3$ | H | CH$_3$ | 2,5-(CH$_3$)$_2$C$_6H_3CH_2$ | H |
| 109 | H | H/COOCH$_2C_6H_3$(CH$_3$)$_2$ | H | CH$_3$ | i-$C_4H_9$ | H | CH$_3$ | $C_{18}H_{37}$ | H |
| 110 | H | H/COO[3-(2-CH$_3$)-1$C_3H_3$] | H | CH$_3$ | H | 5,6-(CH$_3$)$_2$ | $C_2H_5$ | 3-Cl—$C_6H_4CH_2$ | H |
| 111 | H | H/COOC$_6H_{13}$ | H | CH$_3$ | 2-F—$C_6H_4CH_2$ | H | CH$_3$ | CH$_3$ | 6-NO$_2$ |
| 112 | H | H/COONHC$_6H_{12}$N(CH$_3$)$_2$ | H | $C_2H_5$ | H | H | CH$_3$ | CH$_3$ | $C_2H_5$ | H |

EXAMPLE 113

The use of the compounds of Formulas I through VI and described in Examples 1 through 112 as color forming components in pressure sensitive microencapsulated copying systems is illustrated with reference to the product of Example 1, part B.

A. A mixture of 196 ml of distilled water and 15.0 g of pigskin gelatin was stirred at approximately 50° C. for approximately 45 minutes. There was then added to the mixture a warmed (approximately 50° C.) solution of 49.0 g of alkylated biphenyls and 0.5 g of 3-[2,4-bis(-diethylamino)phenyl]-3-(1-ethyl-2-methyl-3-indolyl)phthalide, prepared as described above in Example 1, part B. The resulting solution was stirred for approximately fifteen minutes. A second solution of 81.0 ml of distilled water and 10.0 g of gum arabic was then prepared and warmed to approximately 50° C. for approximately one hour.

B. The two solutions, the first containing water, gelatin, alkylated biphenyls and the product, and the second containing water and gum arabic were mixed and the pH adjusted to 9 by the addition of approximately 0.7 ml of 20 percent aqueous sodium hydroxide. The resulting mixture was transferred to a larger reactor equipped with a variable speed one-half horsepower Eppenbach Homo-Mixer (Gifford-Wood Co., Hudson, N.Y.) and there was added over a period of two to three minutes 650 ml of distilled water which had been heated to 50° C. With the stirrer running at an applied voltage of between 20 to 25 volts there was slowly added sufficient ten percent aqueous acetic acid to set the pH at 4.5, this being the point where coacervation was initiated. The stirrer speed was increased by raising the applied voltage to approximately thirty volts and approximately four drops of 2-ethylhexanol were added to suppress foaming. After approximately twenty minutes, a sample of the suspension was examined microscopically and found to have stabilized in the range of 20 to 25 microns particle size whreupon an external ice/water bath was immediately placed around the reactor containing the suspension. At approximately 20° C., the agitation speed was reduced by decreasing the applied voltage to the range of 20 to 25 volts. Cooling was continued and at approximately 15° C., 10.0 ml of glutaraldehyde was added over a period of five minutes. When the internal temperature reached 10° C., the agitation speed was further reduced by lowering the applied voltage to approximately 20 volts and these conditions maintained for approximately thirty minutes. At this time, the Eppenbach Homo-Mixer was replaced with a conventional blade type laboratory agitator and the suspension was stirred an additional three hours during which period the temperature was allowed to warm to room temperature. The microencapsulated product was isolated by pouring the slurry through an ASTM #18 stainless steel sieve to remove any large agglomerates and then collecting the capsules by filtration. The collected capsules were washed successively with four 100 ml portions of distilled water each and stored as a water wet pulp. A sample of the pulp analyzed by drying in vacuo at 80° C. was found to consist of 37.5 percent solids.

C. To 125 ml of distilled water, 10.6 g of oxidized corn starch was added over a period of ten to fifteen minutes with stirring. This mixture was heated to a temperature in the range of 70°-80° C. and maintained until all the starch dissolved. The starch solution was cooled to ambient temperature and there was added 100 g of the capsule-containing water wet pulp from part B above and 43.0 ml of distilled water. The capsules and starch solution were mixed at room temperature using an Eppenbach Homo-Mixer set at an applied voltage of 25 volts for five minutes and then at an applied voltage of 30 volts for an additional five minutes to complete the suspension of the capsules in the starch solution.

D. The stock starch-microcapsule suspension prepared in part C above was coated on paper sheets to a thicknes of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep blue-colored image promptly formed. The developed image exhibited good lightfastness when exposed to daylight or to a daylignt fluorescent lamp for extended periods.

When evaluated in a duplicating system prepared and tested as described above, the product of Example 1, part C, 3-[2,4-bis(dimethylamino)phenyl]-3-(1-ethyl-2l-methyl-3-indolyl)-phthalide produced a grape-colored developed image.

EXAMPLE 114

The use of the compounds of Formulas I through VI and described in Examples 1 through 112 as color forming components in pressure sensitive microencapsulated copying systems is similarly illustrated with reference to the product of Example 23.

A. A mixture of 196 ml of distilled water and 15.0 g of pigskin gelatin was stirred at approximately 50° C. for approximately 45 minutes. There was then added to the mixture a warmed (approximately 50° C.) solution of 49.0 g of alkylated biphenyls and 1.0 g of 3-(2-ethoxy-4-diethylaminophenyl)-3-(1-ethyl-2-methyl-3-indolyl)-5/6-ethoxycarbonylphthalide prepared as described above the Example 23. The resulting solution was stirred for approximately fifteen minutes. A second solution of 81.0 ml of distilled water and 5.0 g of carboxymethylcellulose was then prepared and warmed to approximately 50° C. for approximately one hour.

B. The two solutions, the first containing water, gelatin, alkylated biphenyls and the product, and the second containing water with carboxymethylcellulose were mixed by means of an Eppenbach Homo-Mixer (Gifford-Wood Co., Hudson, N.Y.). The pH was adjusted to 6.5 by the addition of approximately 0.7 ml of 20 percent aqueous sodium hydroxide. To the resultant mixture was added over a period of two to three minutes 650 ml of distilled water which had been heated to 50° C. With the stirrer running at an applied voltage of between 35 to 40 volts there was slowly added sufficient ten percent aqueous acetic acid to set the pH at 4.5, this being the point where coacervation was initiated. Four drops of 2-ethylhexanol were added to suppress foaming. After approximately twenty minutes an external ice/water bath was placed around the reactor containing the suspension. Cooling was continued and at approximately 15° C., 10.0 ml of glutaraldehyde was added over a period of five minutes. When the internal temperature reached 10° C., the Eppenbach Homo-MIxer was replaced with a conventional blade type laboratory agitator and the thus prepared suspension of microcapsules was stirred an additional three hours during which period the temperature was allowed to warm to room temperature.

C. The microcapsule suspension prepared as described in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep blue-colored image promptly formed. The developed image exhibited good lightfastness when exposed to daylight or to a daylight fluorescent lamp for extended periods.

When evaluated in a duplicating system prepared and tested as described above, the product of Example 29, 3-(4-dimethylaminophenyl)-3-(1-ethyl-2-methyl-3-indolyl)-5/6-ethoxycarbonylphthalide, produced a blue-colored developed image; the product of Example 34, 3-(2-methyl-4-diethylaminophenyl)-3-(1-ethyl-2-methyl-3-indolyl)-5/6-ethoxycarbonylphthalide, produced a turquoise-colored developed image; the product of Example 39B, 3,3-bis(1-ethyl-2-methyl-3-indolyl)-5/6-methoxycarbonylphthalide, produced a deep red-colored developed image; the product of Example 2B, 3-[2,4-bis(dimethylamino)phenyl]-3-(1-ethyl-2-methyl-3-indolyl)-4,5,6,7-tetrachlorophthalide, produced a deep grape-colored developed image; the product of Example 3B, 3-[2,4-bis(dimethylamino)phenyl]-3-(1-ethyl-2-methyl-3-indolyl)-6-nitrophthalide, produced a blue-black-colored image.

EXAMPLE 115

When evaluated in a carbonless duplicating system by proceeding in a manner similar to that described in Example 114 above, except that soy oil was used in places of alkylated biphenyls, the product of Example 20, 3-[2,4-bis(dimethylamino)phenyl]-3-(1-ethyl-2-methyl-3-indolyl)-5/6-n-octyloxycarbonylphthalide, produced a grape-colored developed image; and the product of Example 46, 3,3-bis(1-ethyl-2-methyl-3-indolyl)-5/6-n-octyloxycarbonylphthalide, produced a deep red-colored developed image.

EXAMPLE 116

Following a procedure similar to that described in Example 114 but using kerosene instead of alkylated biphenyls for evaluation in a carbonless duplicating system, the product of Example 26, 3-(2-ethoxy-4-diethylaminophenyl)-3-(1-ethyl-2-methyl-3-indolyl)-5/6-hexadecyloxycarbonylphthalide, produced a deep blue-colored developed image.

EXAMPLE 117

The utility of the phthalides of Formulas I to IV whose preparations are described in the foregoing examples as color forming components in thermal marking systems is illustrated by the incorporation and testing of the compound of Example 22B, 3-(2-ethoxy-4-diethylaminophenyl)-3-(1-ethyl-2-methyl-3-indolyl)-5/6-methoxycarbonylphthalide in a thermal sensitive marking paper. The test paper was prepared by a procedure similar to that described in U.S. Pat. No. 3,539,375.

A. A mixture of 2.0 g of 3-(2-ethoxy-4-diethylaminophenyl)-3-(1-ethyl-2-methyl-3-indolyl)-5/6-methoxycarbonylphthalide, 8.6 g of a ten percent aqueous solution of polyvinyl alcohol (approximately 99 percent hydrolyzed), 3.7 g of water and 31.6 g of 1/16 inch diameter zirconium grinding beads was charged into a container which was placed in a mechanical shaker. Shaking was effected for one hour. The zirconium beads were then removed by straining the mixture throught a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining throught a No. 40 sieve.

C. A coating composition was prepared by mixing 2.1 g of the slurry from A and 47.9 g of the slurry from B. The mixture was then uniformly coated on sheets of paper at thicknesses of approximately 0.003 inch and the coated sheets air-dried. The coated paper was tested by tracing a design on the coated side of the paper placed on a smooth flat surface with a stylus heated to approximately 125° C. A deep blue-colored image corresponding to the traced design promptly developed.

When evaluated in thermal marking paper prepared and tested as described above, the product of Example 39B, 3,3-bis(1-ethyl-2-methyl-3-indolyl)-5/6-methoxycarbonylphthalide, produced a violet-colored image; the product of Example 21, 3-[2,4-bis(dimethylamino)phenyl]-3-(1-ethyl-2-methyl-3-indolyl)-5/6-phenylmethoxycarbonylphthalide, produced a grape-colored image; the product of Example 28B, 3-(4-dimethylaminophenyl)-3-(1-ethyl-2-methyl-3-indolyl)-5/6-methoxycarbonylphthalide, produced a blue-colored image; the product of Example 33B, 3-(2-methyl-4-diethylaminophenyl)-3-(1-ethyl-2-methyl-3-indolyl)-5/6-methoxycarbonylphthalide, produced a turquoise-colored image; the product of Example 1B, 3-[2,4-bis(diethylamino)phenyl]-3-(1-ethyl-2-methyl-3-indolyl)phthalide, produced a blue-black-colored image; the product of Example 1C, 3-[2,4-bis(dimethylamino)phenyl]-3-(1-ethyl-2-methyl-3-indolyl)phthalide, produced a grape-colored image; the product of Example 2B, 3-[2,4-bis(dimethylamino)phenyl]-3-(1-ethyl-2-methyl-3-indolyl)-4,5,6,7-tetrachlorophthalide, produced a deep grape-colored developed image; the product of Example 3B, 3-[2,4-bis(dimethylamino)phenyl]-3-(1-ethyl-2-methyl-3-indolyl)-6-nitrophthalide, produced a blue-black-colored image.

We claim:

1. A pressure-sensitive carbonless duplicating system or thermal marking system containing as a color-forming substance a 3-X-3-Z-4-R°-5-R$^1$-6-R$^2$-7-R$^3$-phthalide of the formula

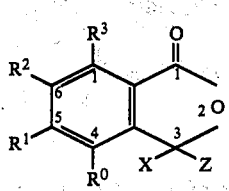

wherein:
R°, R$^1$, R$^2$ and R$^3$ each represent hydrogen or halo or when R°, R$^3$ and one of R$^1$ and R$^2$ are each hydrogen, the other of R$^1$ and R$^2$ represents

in which B represents -OY or

wherein
Y is hydrogen, an alkali metal cation, an ammonium cation, a C$_1$ to C$_{18}$ mono-, di- or trialkylammonium cation, C$_1$ to C$_{18}$ alkyl, C$_2$ to C$_{18}$ alkenyl, benzyl or benzyl substituted in the benzene ring thereof by C$_1$ to C$_{12}$ alkyl, halo or C$_1$ to C$_8$ alkoxy;
Y' is hydrogen or C$_1$ to C$_{18}$ alkyl;
Y" is hydrogen, C$_1$ to C$_{18}$ alkyl or C$_4$ to C$_{12}$ N,N-dialkylaminoalkyl;
X represents a monovalent moiety selected from the class having the formulas

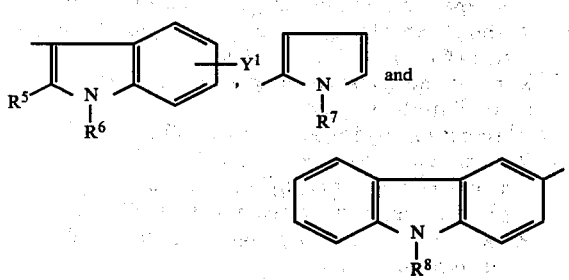

Z represents a monovalent moiety selected from the class having the formulas

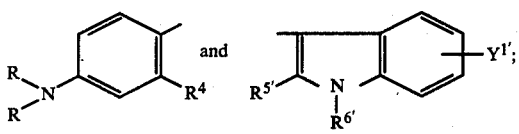

in which
R represents non-tertiary C$_1$ to C$_4$ alkyl, benzyl or benzyl substituted in the benzene ring by one or two of halo or C$_1$ to C$_3$ alkyl,
R$^4$ represents acetamido, dialkylamino in which alkyl is non-tertiary C$_1$ to C$_4$ alkyl, and when one of R$^1$ or R$^2$ represents said

R$^4$ further represents hydrogen, C$_1$ to C$_3$ alkyl, C$_1$ to C$_4$ alkoxy or halo,
R$^5$ and R$^{5'}$ represent hydrogen, C$_1$ to C$_3$ alkyl or phenyl,
R$^6$ and R$^{6'}$ represent hydrogen, C$_1$ to C$_{18}$ alkyl, C$_2$ to C$_4$ alkenyl, benzyl or benzyl substituted in the benzene ring by one or two of halo or C$_1$ to C$_3$ alkyl,
R$^7$ and R$^8$ represent hydrogen, C$_1$ to C$_3$ alkyl or phenyl, and
Y$^1$ and Y$^{1'}$ represent one or two of hydrogen, C$_1$ to C$_3$ alkyl, C$_1$ to C$_3$ alkoxy, halo or nitro
with the provisos (i) that X and Z can both simultaneously represent monovalent indolyl moieties only when one of R$^1$ and R$^2$ represents said

and (ii) X represents a pyrrolyl or a carbazolyl moiety only when Z represents a 2-R$^4$-4-N(R)$_2$-phenyl moiety.

2. A pressure-sensitive carbonless duplicating system according to claim 1 comprising a support sheet coated on one side with a layer of pressure-rupturable microcapsules containing a liquid solution of the color-forming substance.

3. A thermal marking system according to claim 1 comprising a support sheet coated on one side with a layer containing a mixture of the color-forming substance and an acidic developer arranged such that application of heat will produce a mark-forming reaction between the color-forming substance and the acidic developer.

4. A hectographic copying system comprising a support sheet coated on one side with a layer containing a color-forming substance comprising a compound according to claim 1 wherein R°, R$^3$ and one of R$^1$ and R$^2$ are each hydrogen, the other of R$^1$ and R$^2$ represents

wherein Y is an alkali metal cation, an ammonium cation or a C$_1$ to C$_{18}$ mono-, di- or trialkylammonium cation.

5. A pressure-sensitive carbonless duplicating system or thermal marking system according to claim 1 containing as the color-forming substance a 3-[2-R$^4$-4-N(R)$_2$-phenyl]-3-[(1-R$^6$-2-R$^5$-5/6-Y$^1$)-3-indolyl]-4-R°-5-R$^1$-6-R$^2$-7-R$^3$-phthalide wherein R, R°, R$^1$, R$^2$, R$^3$, R$^4$, R$^5$, R$^6$ and Y$^1$ have the same respective meanings given in claim 1.

6. A pressure-sensitive carbonless duplicating system or thermal marking system according to claim 5 containing as a color-forming substance 3-[2,4-bis(dimethylamino)phenyl]-3-(1-ethyl-2-methy-3-indolyl)phthalide.

7. A pressure-sensitive carbonless duplicating system or thermal marking system according to claim 5 containing as a color-forming substance 3-[2,4-bis(diethylamino)phenyl]-3-(1-ethyl-2-methyl-3-indolyl)phthalide.

8. A pressure-sensitive carbonless duplicating system or thermal marking system according to claim 5 containing as a color-forming substance 3-[2,4-bis(dimethylamino)phenyl]-3-(1-ethyl-2-methyl-3-indolyl)-4,5,6,7-tetrachlorophthalide.

9. A pressure-sensitive carbonless duplicating system or thermal marking system according to claim 5 containing as a color-forming substance 3-(2-ethoxy-4-diethylaminophenyl)-3-(1-ethyl-2-methyl-3-indolyl)-5/6-ethoxycarbonylphthalide.

10. A pressure-sensitive carbonless duplicating system or thermal marking system according to claim 5 containing as a color-forming substance 3-(2-ethoxy-4-diethylaminophenyl)-3-(1-ethyl-2-methyl-3-indolyl)-5/6-hexadecyloxycarbonylphthalide.

11. A pressure-sensitive carbonless duplicating system or thermal marking system according to claim 1 containing as the color-forming substance a 3-[(1-$R^6$-2-$R^5$-5/6-$Y^1$)-3-indolyl]-3-[(1-$R^{6'}$-2-$R^{5'}$-5/6-$Y^{1'}$-3-indolyl]-4-$R^°$-5-$R^1$-6-$R^2$-7-$R^3$-phthalide wherein $R^°$, $R^1$, $R^2$, $R^3$, $R^5$, $R^6$, $R^{5'}$, $R^{6'}$, $Y^1$ and $Y^{1'}$ have the same respective meanings given in claim 1.

12. A pressure-sensitive carbonless duplicating system or thermal marking system according to claim 11 containing as the color-forming substance 3,3-bis(1-ethyl-2-methyl-3-indolyl)-5/6-methoxycarbonylphthalide.

13. A pressure-sensitive carbonless duplicating system or thermal marking system according to claim 11 containing as the color-forming substance 3,3-bis(1-ethyl-2-methyl-3-indolyl)-5/6-n-octyloxycarbonylphthalide.

14. A pressure-sensitive carbonless duplicating system or thermal marking system according to claim 11 containing as the color-forming substance 3,3-bis(1-ethyl-2-methyl-3-indolyl)-5/6-n-hexadecyloxycarbonylphthalide.

15. A pressure-sensitive carbonless duplicating system or thermal marking system containing as a color-forming substance a 3-X-3-Z-4-$R^°$-5-$R^1$-6-$R^2$-7-$R^3$-phthalide of the formula

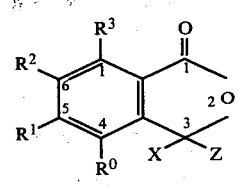

wherein:
$R^°$, $R^3$ and one of $R^1$ and $R^2$ are each hydrogen, the other of $R^1$ and $R^2$ represents nitro, amino, acetamido or dialkylamino wherein alkyl is non-tertiary $C_1$ to $C_4$ alkyl;
X represents a monovalent moiety selected from the class having the formulas

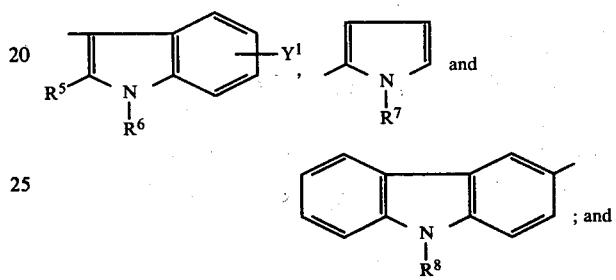

Z represents a monovalent moiety having the formula

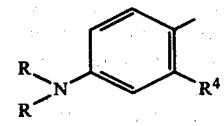

in which
R represents non-tertiary $C_1$ to $C_4$ alkyl, benzyl or benzyl substituted in the benzene ring by one or two of halo or $C_1$ to $C_3$ alkyl,
$R^4$ represents dialkylamino in which alkyl is non-tertiary $C_1$ to $C_4$ alkyl,
$R^5$ represents hydrogen, $C_1$ to $C_3$ alkyl or phenyl,
$R^6$ represents hydrogen, $C_1$ to $C_{18}$ alkyl, $C_2$ to $C_4$ alkenyl, benzyl or benzyl substituted in the benzene ring by one or two of halo or $C_1$ to $C_3$ alkyl,
$R^7$ and $R^8$ represent hydrogen, $C_1$ to $C_3$ alkyl or phenyl, and
$Y^1$ represents one or two of hydrogen, $C_1$ to $C_3$ alkyl, $C_1$ to $C_3$ alkoxy, halo or nitro.

* * * * *

UNITED STATES PATENT AND TRADEMARK OFFICE
CERTIFICATE OF CORRECTION

PATENT NO. : 4,189,171

DATED : February 19, 1980

INVENTOR(S) : Nathan N. Crounse and Paul J. Schmidt

It is certified that error appears in the above-identified patent and that said Letters Patent is hereby corrected as shown below:

Column 5, line 47, "$R^6$" should be followed by "and $R^{6'}$".

Column 5, line 50, "$Y^1$" should be followed by "and $Y^{1'}$".

Column 5, line 66, "$R^4$-N(R)$_2$-phenyl]" should read -- $R^4$-4-N(R)$_2$-phenyl] --.

Signed and Sealed this

Third Day of December 1985

[SEAL]

Attest:

DONALD J. QUIGG

Attesting Officer     Commissioner of Patents and Trademarks